(12) United States Patent
Pradelles et al.

(10) Patent No.: US 11,806,316 B2
(45) Date of Patent: Nov. 7, 2023

(54) FOOD SUPPLEMENT

(71) Applicant: MICROPHYT, Baillargues (FR)

(72) Inventors: Rémi Pradelles, Montpellier (FR); Antoine Delbrut, Montpellier (FR)

(73) Assignee: MICROPHYT, Baillargues (FR)

( * ) Notice: Subject to any disclaimer, the term of this patent is extended or adjusted under 35 U.S.C. 154(b) by 0 days.

(21) Appl. No.: 16/798,609

(22) Filed: Feb. 24, 2020

(65) Prior Publication Data

US 2020/0268816 A1    Aug. 27, 2020

(30) Foreign Application Priority Data

Feb. 22, 2019    (FR) ...................................... 19/01820

(51) Int. Cl.
| | | |
|---|---|---|
| *A61K 36/02* | (2006.01) | |
| *A61K 31/336* | (2006.01) | |
| *A61K 31/575* | (2006.01) | |
| *A61K 47/44* | (2017.01) | |

(52) U.S. Cl.
CPC ............ *A61K 36/02* (2013.01); *A61K 31/336* (2013.01); *A61K 31/575* (2013.01); *A61K 47/44* (2013.01)

(58) Field of Classification Search
None
See application file for complete search history.

(56) References Cited

U.S. PATENT DOCUMENTS

2010/0233746 A1    9/2010    Sonntag et al.

FOREIGN PATENT DOCUMENTS

| JP | 2018064553 | * | 4/2018 |
| WO | 2012156970 A1 | | 11/2012 |
| WO | 2013032333 A1 | | 3/2013 |

OTHER PUBLICATIONS

Loeffler et al., Plant Physiology, 2005, vol. 137, 328-340.*

* cited by examiner

*Primary Examiner* — Michael V Meller
(74) *Attorney, Agent, or Firm* — CANTOR COLBURN LLP

(57) ABSTRACT

A composition comprising at least 50 mg/g of one or several omega-3 type fatty acid(s), at least 10 mg/g of one or several xanthophyll(s), at least 1 mg/g of one or several sterol(s) and at least 2 μg/g of one or several phycoprostane(s), and its applications in particular as a food supplement in the prevention of the apparition of cognitive disorders.

5 Claims, 12 Drawing Sheets

[Fig. 1]
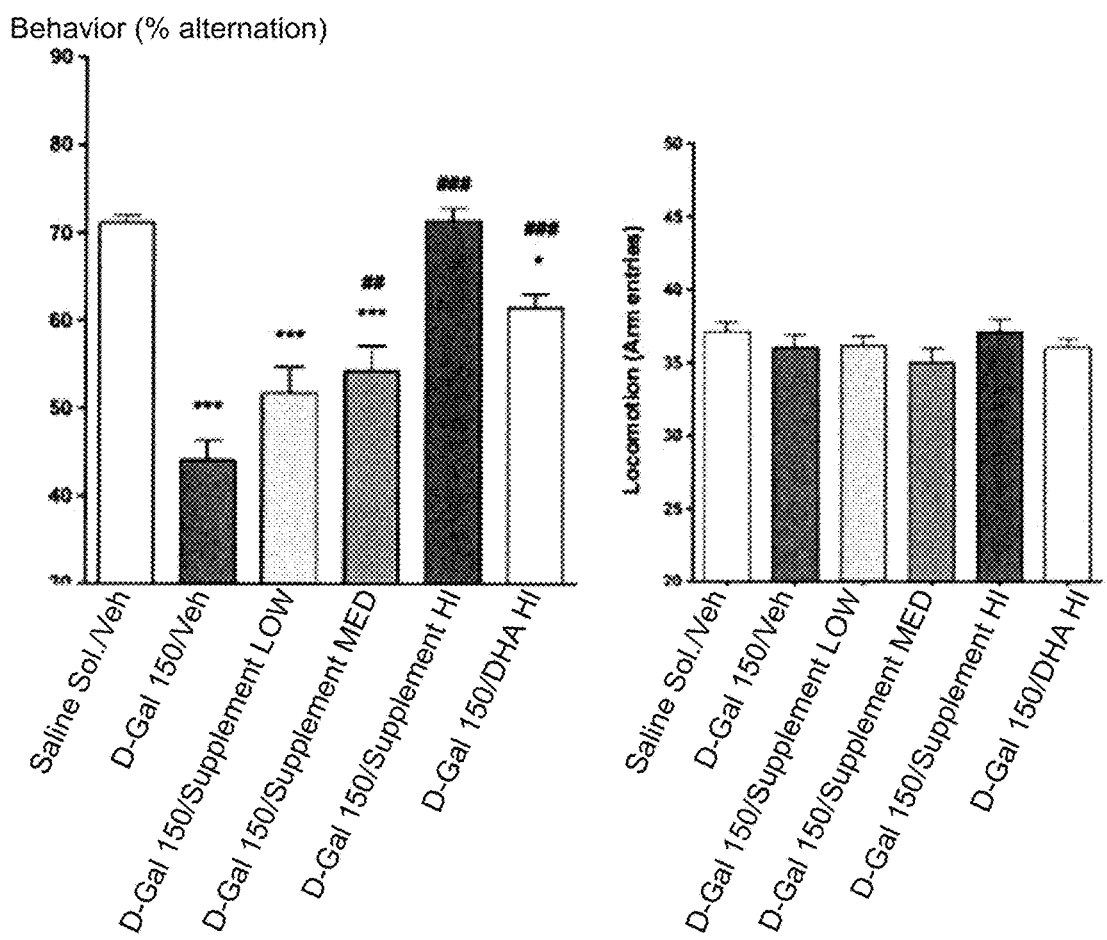

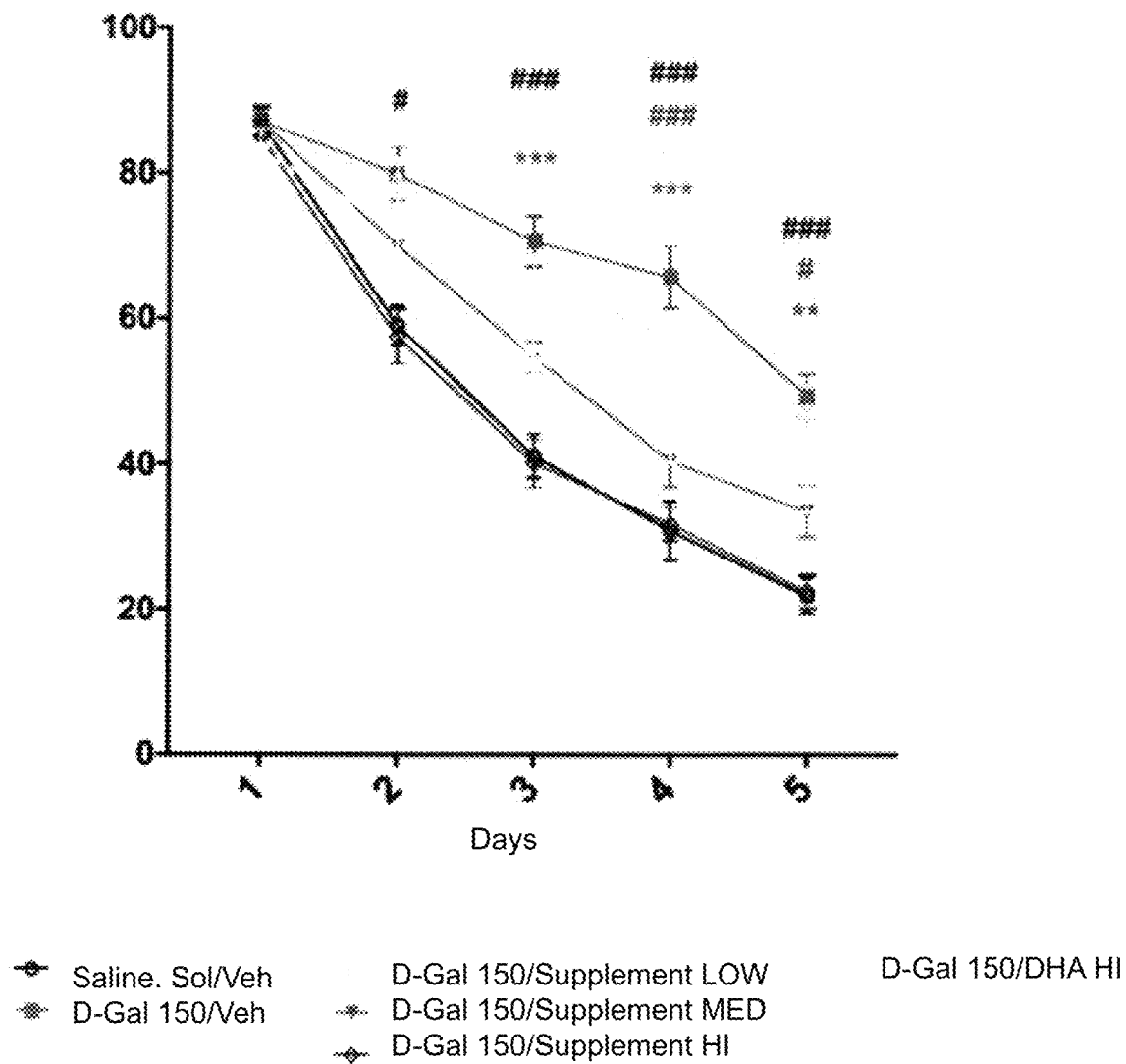
[Fig. 2]

[Fig. 3]
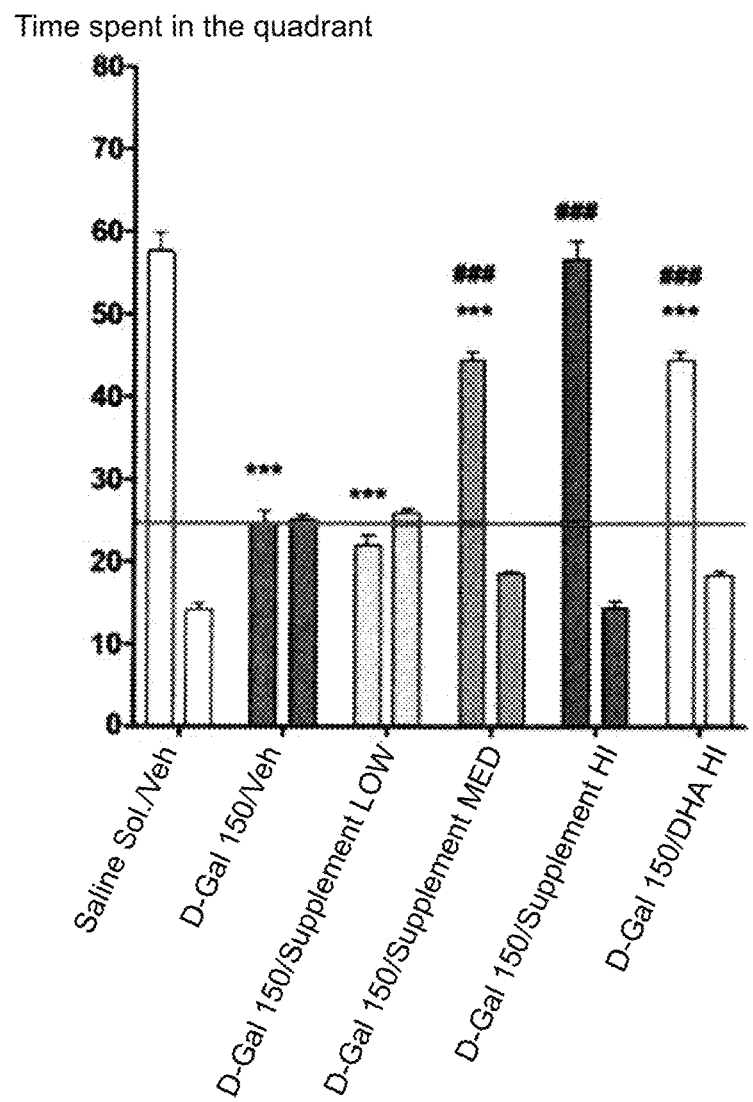

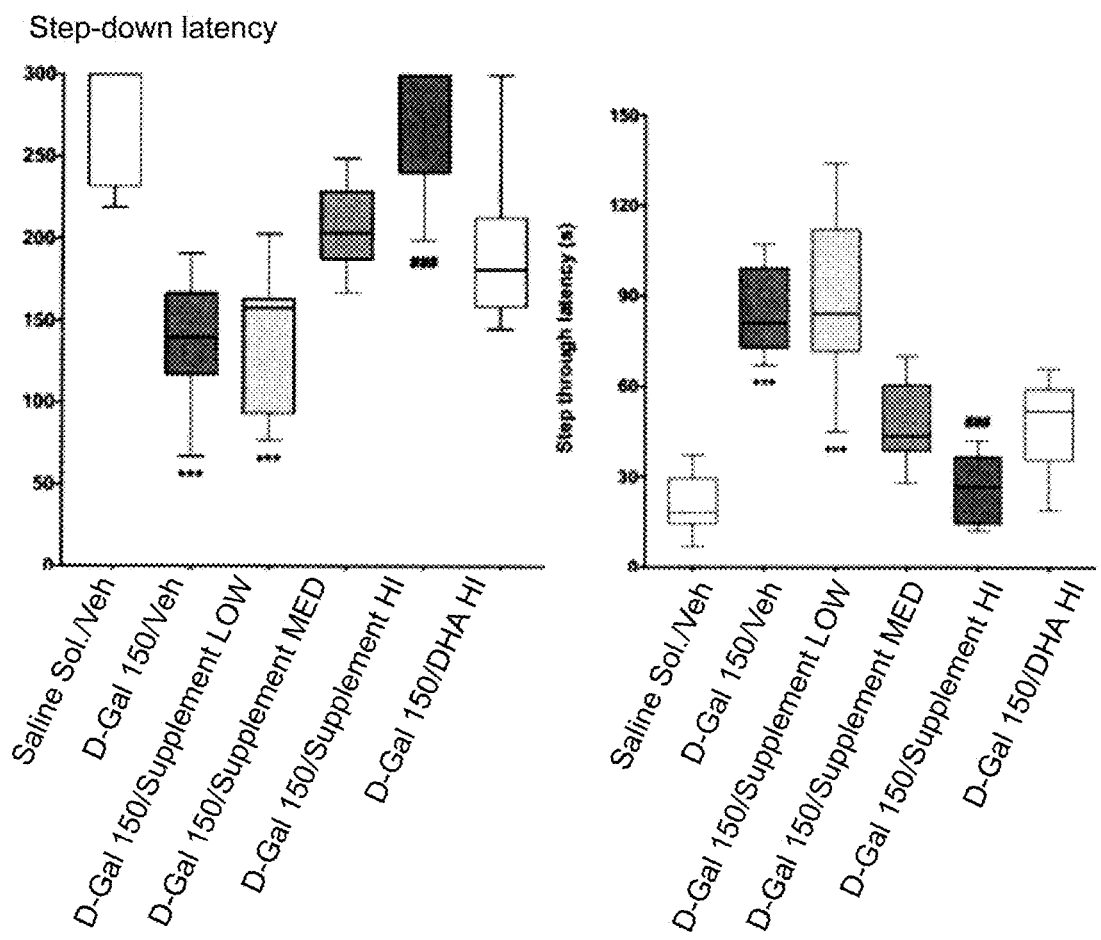
[Fig. 4]

[Fig. 5]
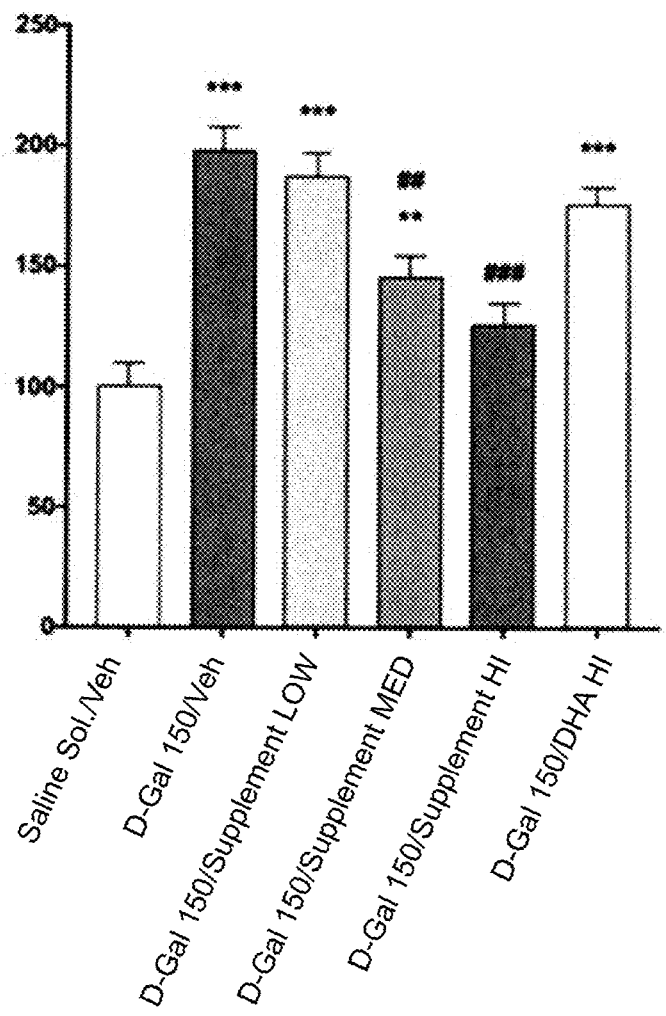

[Fig. 6]
TNF-α content (% of Veh/Veh)
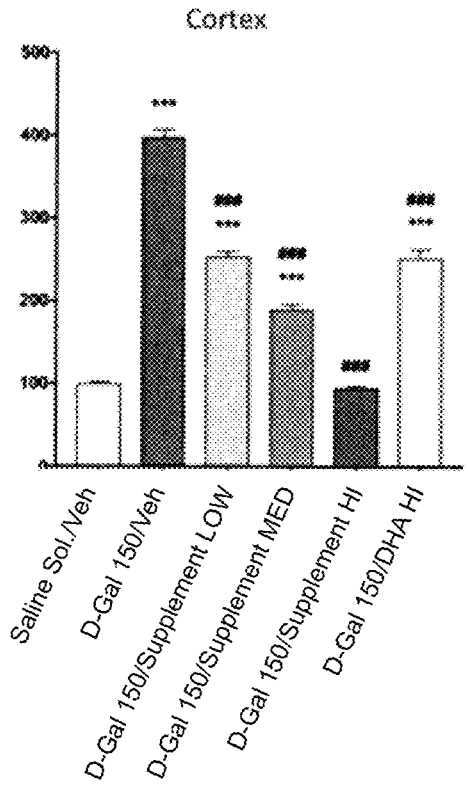
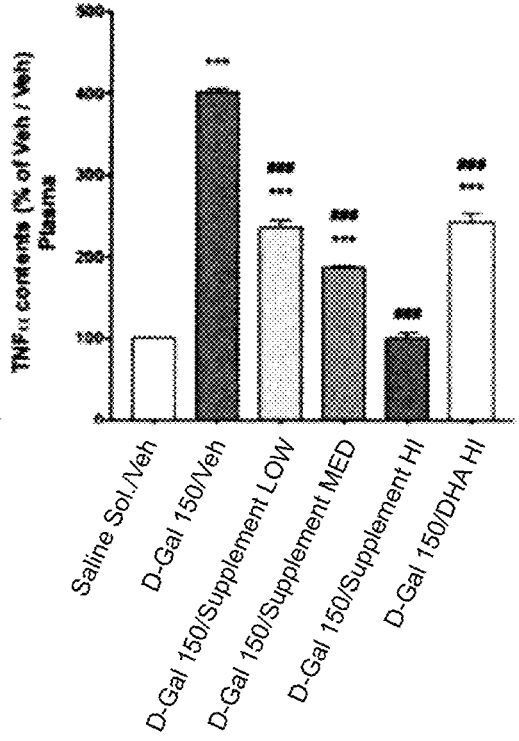
[Fig. 7]
IL-6 content (% of Veh/Veh)
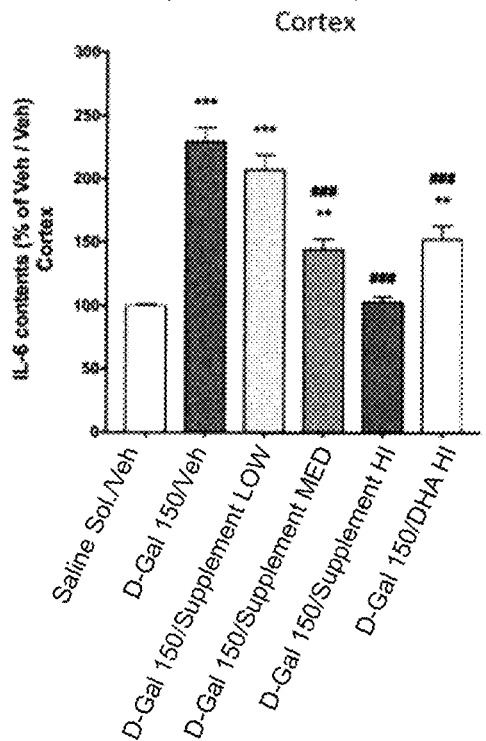
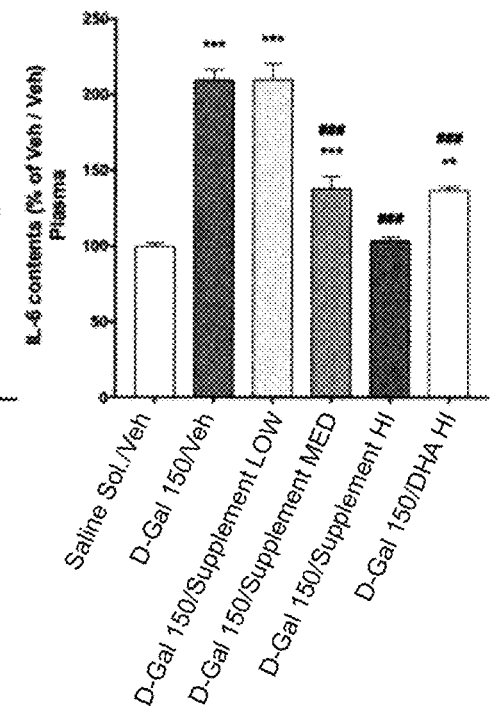

[Fig. 8]
Anxiety (% of locomotion in the peripheral area of the test area)
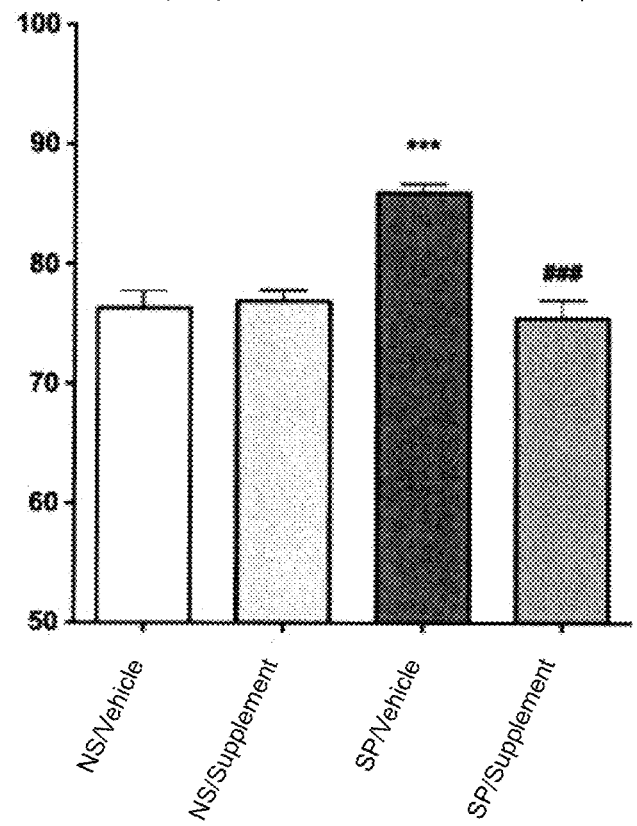

[Fig. 9]
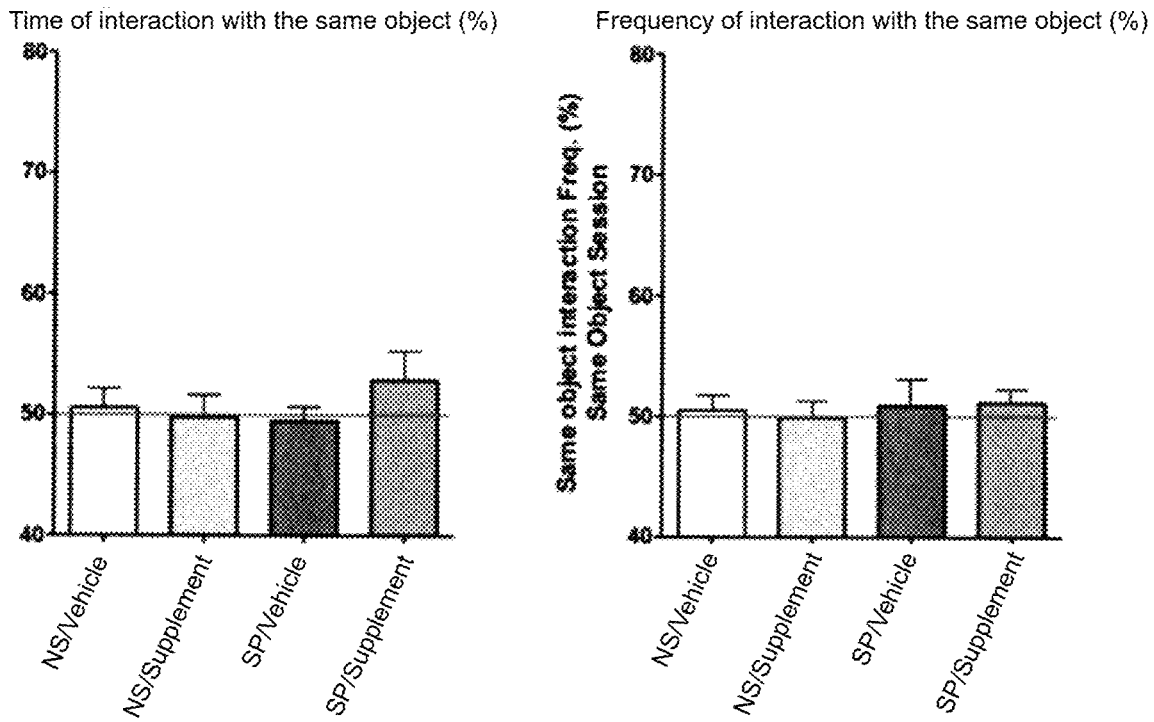
[Fig. 10]
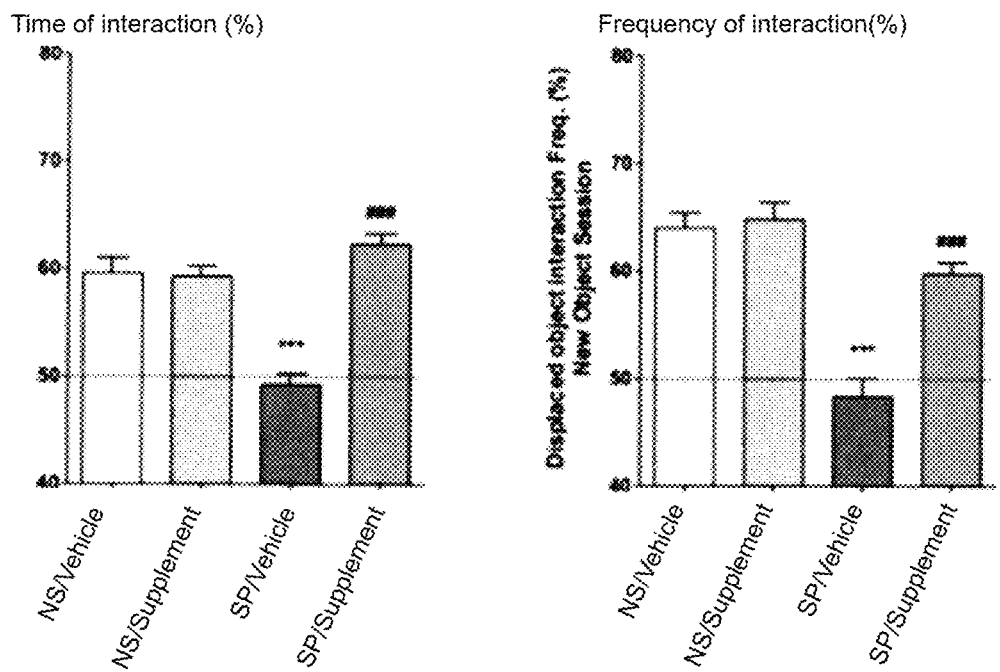

[Fig. 11]
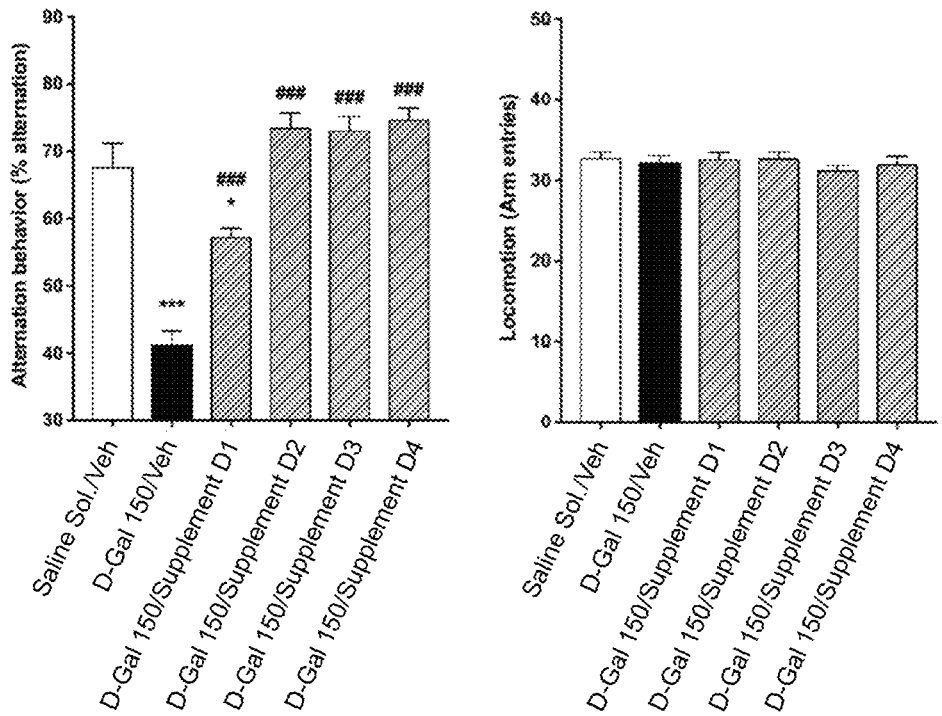
[Fig. 12]
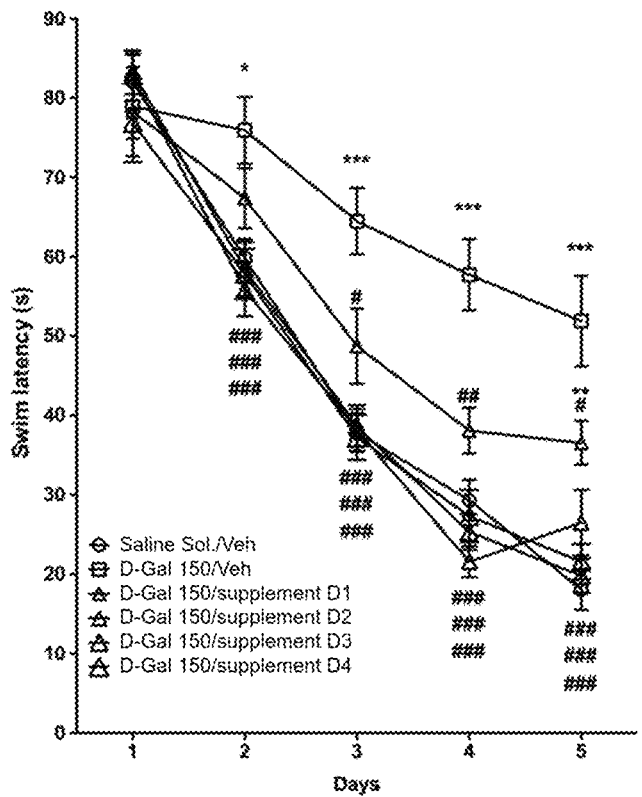

[Fig. 13]
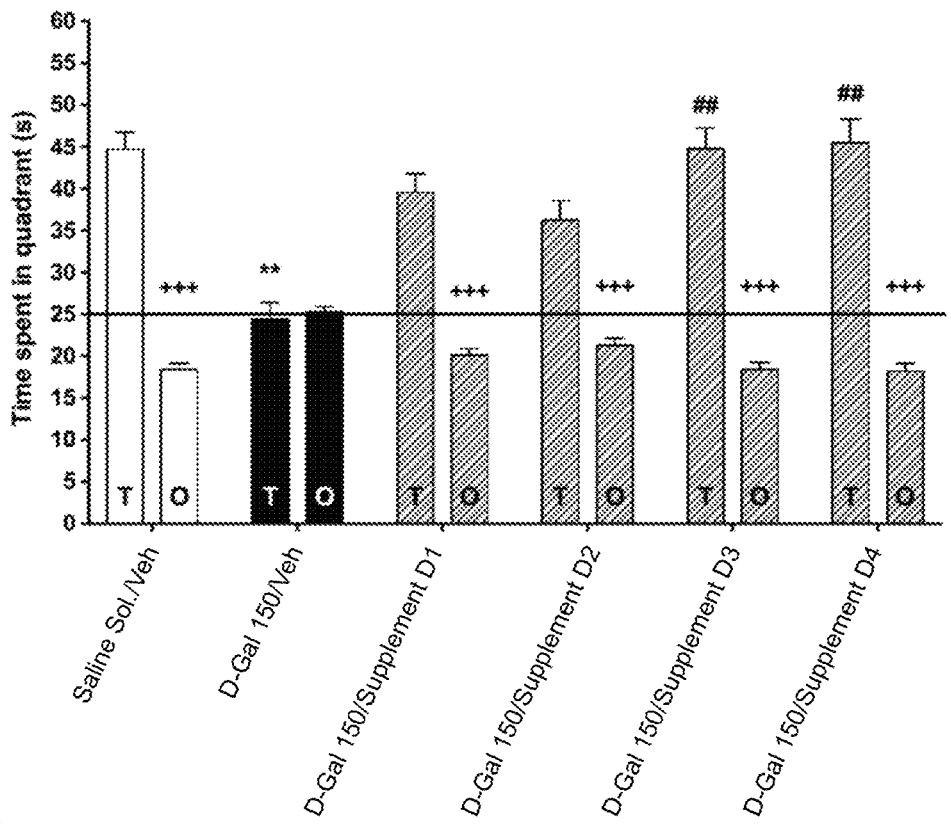
[Fig. 14]
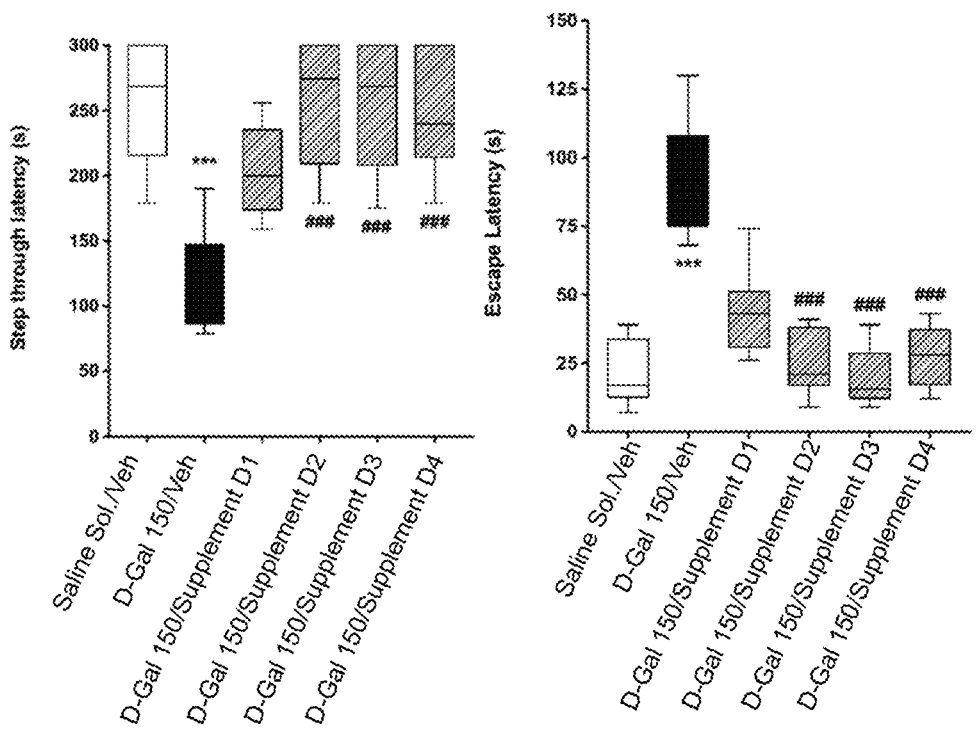

[Fig. 15]
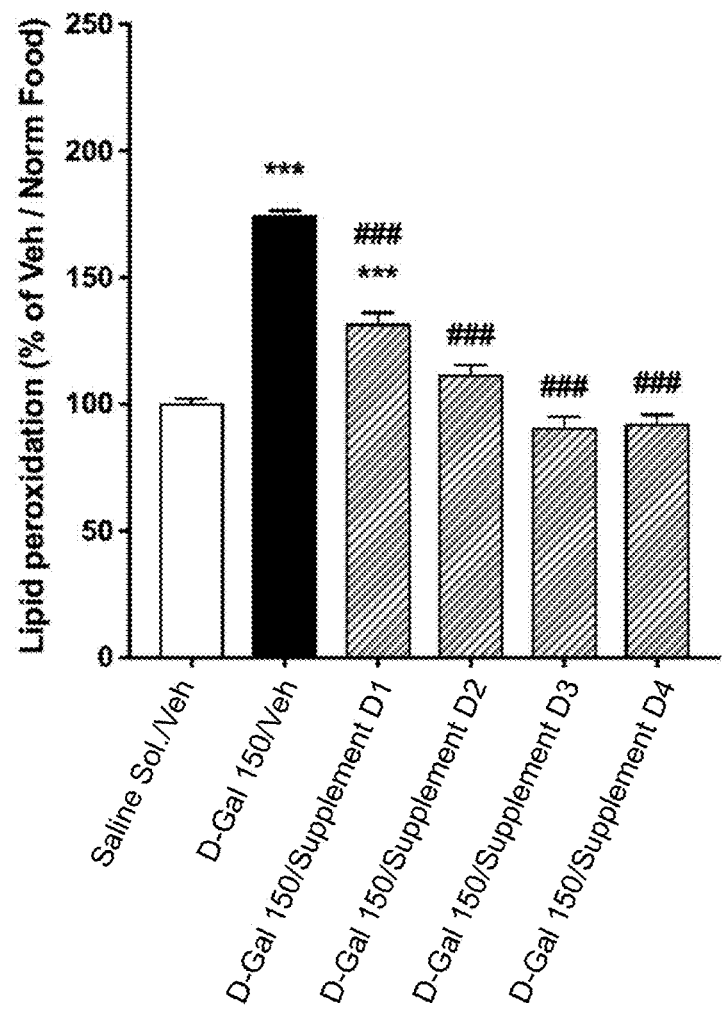

[Fig. 16]
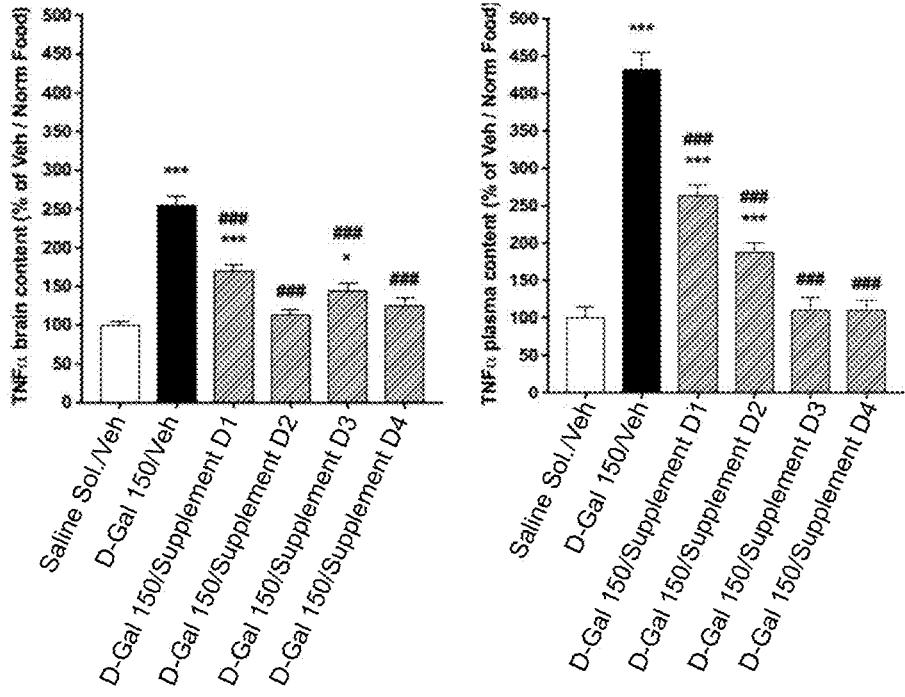
[Fig. 17]
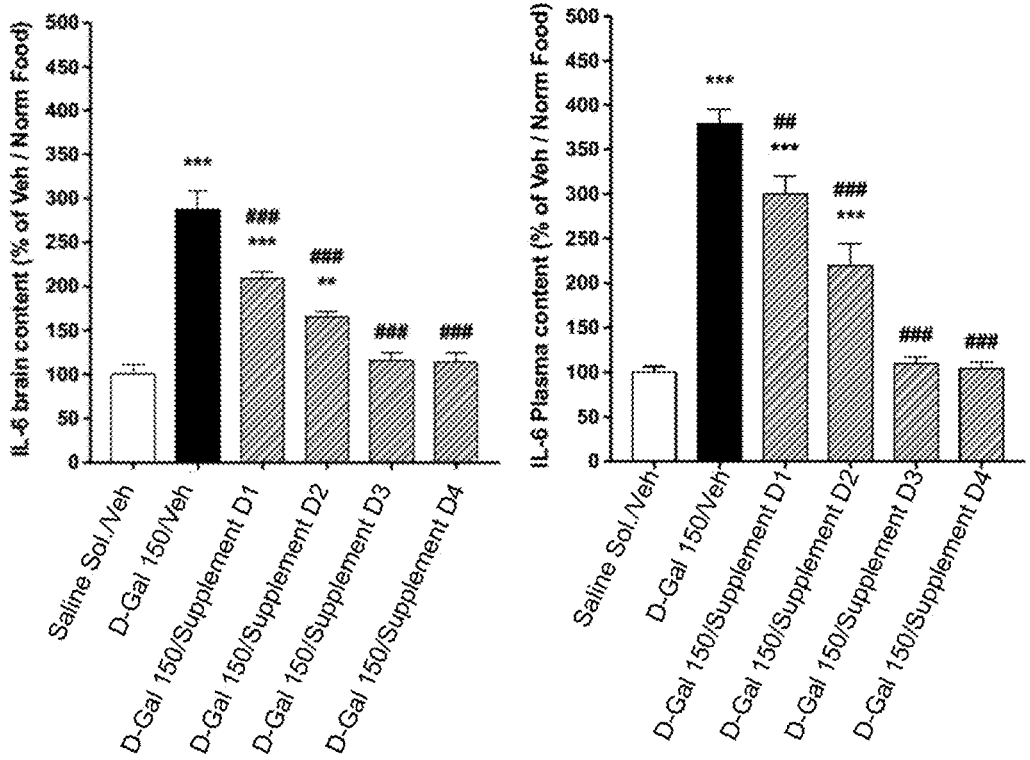

FOOD SUPPLEMENT

CROSS REFERENCE TO RELATED APPLICATION

This application is related to and claims the benefit of French Patent Application No. 19/01820 filed on 22 Feb. 2019 of which said application is herein incorporated by reference in its entirety.

TECHNICAL FIELD

The present disclosure concerns a composition, as well as a food supplement based on fatty acids and xanthophylls and the applications thereof in particular to prevent the apparition of cognitive disorders in humans or animals.

BACKGROUND

The cognitive processes are defined as all cerebral functions allowing acquiring, processing, memorizing and using data originating from the environment in order to maximize the advantages and minimize the drawbacks of the external constraints. Thus, the cognitive processes are implemented during phases involving reasoning (giving rise to planning, organization, judgment), perception, recognition, language, emotions, memory and learning.

Light cognitive disorders, or cognitive fragilities, are defined as alterations of the cognitive functions without dementia. From a clinical perspective, these disorders are associated to a 0.5 score in the context of an assessment via the CDR (Cognitive Drug Research Computerized Assessment System) test.

Amongst these cognitive disorders, a cognitive decline associated with ageing and cognitive alterations induced by a prenatal stress are two phenomena that might intervene throughout the life of an individual.

The age-related cognitive decline is defined as a non-pathological decrease in the cognitive functions such as the speed of information processing, the attentional ability and especially the so-called working (or short-term) memory. These processes result from normal physiological modifications directly related to the age. The age of the start of this decline is still controversial, but given the acceleration of the ageing of the world population, more than 20% of the world population being more than 60 years, and this percentage will be more than 30% in 2050, the age-related cognitive decline is amongst the major issues of these upcoming decades, at global level, and specifically in developed countries, in which it will considerably impact the economy (less autonomy for elderly persons) and public policies.

At the opposite of the age composition pyramid, cognitive disorders may affect infants and young children following a prenatal stress. Indeed, for several years now, the influence of stress during some period of the pregnancy on the cognitive development of the unborn individual has been studied both in humans and in animals. Thus, in animals, mainly in rats, it has been demonstrated that a prenatal stress in the mother would induce a progeny having an altered long-term memory.

It turns out that intense negative stimuli, stress, may induce non-pathological alterations or decreases in the cognitive functions of young children, manifested in an hyperactivity, an attention and memory deficit, language retardation, more difficult temperaments and more generally behavioral alterations such as an anxious behavior, revealing a neurodevelopmental retardation and a decrease in the cognitive abilities.

One amongst the presumed mechanisms of the expression of the prenatal stress into cognitive disorders, is based on the contact of the fetus with large doses of so-called stress hormones, belonging to the family of corticosteroids, such as cortisol. Yet, cortisol crosses the placental barrier and, starting from a determined concentration, the protective mechanisms of the fetus against the corticoids secreted by the mother, are saturated, thereby bringing the fetus in contact with too considerable doses of cortisol which seem to have a negative effect on the cognitive development. Other complementary assumptions explain the relationship between the prenatal stress and the cognitive disorders of the child, have been developed.

The stress concept may be defined according to different perspective such as the biological approach: stress is then a series of metabolic reactions, following one or several exogenous factor(s), inducing physiological or psychological changes (fear, anguish) in the organism. However, the stress concept and its impacts is largely individual-specific, and the response of the individual to a stress is also defined from a psychological perspective. Henceforth, bearing in mind that an event is stressful only retrospectively, because of a reaction that is specific to each individual, or because it may be objectively stressful, it is difficult to act on the sources of prenatal stress. Added to this is the fact that pregnancy induces hormonal and psychological changes increasing the sensitivity of the prospective mother to every event likely to impact the well-being of the unborn infant.

The strictly therapeutic approach of stress or anxiety, in the form of drugs prescription, is dangerous in the case of a pregnant woman: numerous psychotropic drugs for the treatment of psychological disorders or anxiety have teratogenic effects with direct adverse effects on the fetus. This requires an assessment on a case-by-case basis, and this approach is used only in the case of clinical psychological disorders in the pregnant woman and not in the case of so-called subjective stresses.

Thus, there is a major problem relating to the discovery of solutions against the consequences of prenatal stress on cognitive disorders in children or young adults.

Different studies have shown the interest of a nutritional supplementation of so-called essential fatty acids, but also of carotenes and in particular xanthophylls, and even the combination of said fatty acids and said carotenes, to prevent or at least limit the decline of the cognitive functions. Food supplements or drugs have been developed leading to positive results.

Thus, there is known according to the document WO2013/032333A1, a composition based on omega-3 type fatty acids, in particular the eicosapentaenoic acid (EPA) and the docosahexaenoic acid (DHA), asthaxanthin and glycerophospholipids, which is recommended for the prevention or the treatment of different disorders and in particular cognitive disorders. Said ingredients are present in this composition in the form of extracts of microalgae; in a preferred variant of preparation, they are obtained by formulation of two extracts originating from two different algae. The natural origin of the constituents of the composition is a tremendous benefit. Nonetheless, the need for more effective compositions still exists, in particular with regards to the aforementioned issues. Furthermore, it is important to provide methods for preparing such compositions that are simple and replicable.

BRIEF SUMMARY

The disclosure brings in a solution with a composition comprising one or several omega-3 type fatty acid(s) and one or several xanthophyll(s), as well as one or several compound(s) of the family of sterols and one or several phycoprostane(s). It turned out that the combination of at least one sterol and at least one phycoprostane with at least one omega-3 type fatty acid and at least one xanthophyll significantly increases the effectiveness of a composition in the prevention of the apparition of age-related cognitive disorders but also against those associated to a prenatal stress.

A composition of the disclosure comprises:
 at least 50 mg/g of one or several omega-3 type fatty acid(s),
 at least 10 mg/g of one or several xanthophyll(s),
 at least 1 mg/g of one or several sterol(s), and
 at least 2 µg/g of one or several phycoprostane(s).

In a primary indication, a composition of the disclosure may be used as a food supplement. Also, the disclosure concerns a food supplement which comprises at least 50 mg/g of one or several omega-3 type fatty acid(s), at least 10 mg/g of one or several xanthophyll(s), at least 1 mg/g of one or several sterol(s), and at least 2 µg/g of one or several phycoprostane(s).

The disclosure has an essential advantage in that all of the constituents or ingredients hereinabove may be obtained from a natural source and in particular they may be extracted from one or several microalga(e), and preferably from one single microalga. Of course, the constituent(s) or ingredient(s) of a composition or of a food supplement of the disclosure may have a non-natural origin and be provided in the form of chemically synthesized products.

Before disclosing the disclosure in more details, some terms used in the present text are defined.

The term « comprises » in the expression « a composition comprises » or « a food supplement comprises » means that the composition or the supplement may incorporate any additional constituent or more, which is not specifically mentioned, in any form and from any origin whatsoever. It also covers a composition or a supplement that would contain only the listed constituents and consequently the composition or the supplement would consist of said constituents.

A food supplement is defined as one or several foodstuff(s) whose purpose is to complete the normal diet of a human or of an animal, and which constitute a concentrated source of nutrients or other substances having a nutritional or physiological effect alone or in combination; it is generally available in the form of doses, namely the packaging forms such as gel capsules, pastilles, tablets, pills and other similar forms, as well as powder packs, ampoules of liquid, vials fitted with a dropper and the other similar forms of liquid or powder preparations intended to be taken in units measured in a small amount.

Omega-3 type fatty acid(s) are a family of unsaturated fatty acids whose hydrocarbon chain has 4 to 36 atoms of carbon, in general from 14 to 36 atoms of carbon, and whose double bond or whose first double bond, counted starting from the terminal methyl group of the chain, is on the third carbon-carbon bond. The unsaturation(s) may be of the cis or trans type, independently from one another. The most representative acids are the alpha-linolenic acid (ALA), the eicosapentaenoic acid (EPA) and the docosahexaenoic acid (DHA), but the designation « omega-3 type fatty acids » is not restricted thereto. Furthermore, and in particular when the fatty acid(s) are from a natural origin, they may be extracted from algae and be in the form of free molecules but also in a derivative form such as an esterified form, for example in a mono-, di- or tri-esterified form, or in mixtures of these forms.

By xanthophylls, are defined the molecules belonging to the carotenoids including one or several atom(s) of oxygen such as astaxanthin, canthaxanthin, vaucheriaxanthin, lutein, zeaxanthin, diadinoxanthin, neoxanthin, loroxanthin, siphonoxanthin, diatoxanthin, violaxanthin, dinoxanthin, flavoxanthin, α-cryptoxanthin, β-cryptoxanthin and fucoxanthin. In particular, when the xanthophyll(s) are from a natural origin, they may be extracted from algae and be in the form of free molecules but also in a derivative form such as an esterified form of mono- or multi-esters, or in mixtures of these forms.

Sterol(s) are a family of well-known lipids having a sterane core whose $3^{rd}$ position carbon carries a hydroxyl group, the latter may be modified for example by an acetyl group. These include natural sterols or phytosterols, and are grouped in the present text under the term phycosterols. Without limitation, as examples of phytosterols, mention may be made to 24-methylene cholesterol, β-sitosterol, fucosterol, isofucosterol, saringosterol, oxocholesterol acetate, crinosterol, and more particularly brassicasterol, stigmasterol and campesterol.

By phycoprostanes, it should be understood a family of lipids that are structurally of the prostaglandin type, from a natural origin, resulting from non-directly enzymatic oxidations of the fatty acids naturally present within the microalgal biomasses. In particular, these compounds are selected from phytoprostanes, isoprostanes and neuroprostanes, depending on the fatty acid that has undergone the oxidation(s). Thus, these compounds may originate from fatty acids such as the a-linolenic acid (ALA), the arachidonic acid (ARA), the eicosapentaenoic acid (EPA), or the docosahexaenoic acid (DHA). The phytoprostanes are mainly derived from ALA and may be selected from 9-epi-9Flt-PhytoP, ent-16-epi-16-F1t-PhytoP, 9-F1t-PhytoP, ent-16B1t-PhytoP, ent-9L1t-PhytoP, 16(RS)-16-Alt-PhytoP. The isoprostanes are mainly derived from ARA and EPA and may be selected from 15-E2t-IsoP, 15-F2t-IsoP, 15-epi-15-F2t-IsoP, 5-F2t-IsoP, 8(RS)-8-F3t-IsoP. The neuroprostanes are mainly derived from DHA and may be selected from 4-F3t-NeuroP, 10-F4t-NeuroP, 10-epi-10-F4t-NeuroP, 4(RS)-4-F4t-NeuroP, 14(RS)-14-F4t-NeuroP, 20(R)-20-F4t-NeuroP.

By Medium-Chain Triglycerides (MCT), it should be understood esters of glycerol and saturated fatty acids, whose hydrocarbon chain has 6 to 12 atoms of carbon. They are naturally present in coconut palm oil such as coconut oil, palm kernel oil and palm oil, but they may be obtained from other greases or oils.

The present disclosure is described hereinafter in more details and its variants are disclosed.

Advantageously, a composition or a food supplement of the disclosure presents the following features, considered separately or in any combination.

It comprises 50 to 250 mg/g of one or several omega-3 type fatty acid(s), 10 to 50 mg/g of one or several xanthophyll(s), 1 to 20 mg/g of one or several sterol(s) and 2 to 100 µg/g of one or several phycoprostane(s).

It comprises 50 to 200 mg/g of one or several omega-3 type fatty acid(s), 10 to 30 mg/g of one or several xanthophyll(s), 1 to 8 mg/g of one or several sterol(s) and 2 to 50 µg/g of one or several phycoprostane(s).

It comprises 50 to 170 mg/g of one or several omega-3 type fatty acid(s), 10 to 25 mg/g of one or several xanthophyll(s), 1 to 6 mg/g of one or several sterol(s) and 2 to 40 µg/g of one or several phycoprostane(s).

Advantageously, a composition or a food supplement of the disclosure further contains at least one oil as a vehicle or support to facilitate the expression of the active ingredients. Surprisingly, it has been observed that the production of a composition or of a food supplement is facilitated when this oil is selected from medium-chain triglycerides (MCT). In particular, when the active ingredients are obtained from the same microalga extract, an optimum homogenization is observed in such oil. According to one variant, the medium-chain triglycerides (MCT) are from a natural origin and are brought by oil selected from coconut palm oil, palm kernel oil and palm oil; they may also be obtained or derived from such oil.

Hereinafter, preferred formulations of a composition or of a food supplement of the disclosure are presented, these implementations may of course be combined:

the or at least one of the omega-3 type fatty acids is selected from stearidonic acid (SDA), eicosapentaenoic acid (EPA), docosahexaenoic acid (DHA) and mixtures thereof;

the or at least one of the xanthophylls is fucoxanthin;

the or at least one of the sterols is selected from phytosterols;

the or at least one of the phycoprostanes is selected from phytoprostanes, isoprostanes and neuroprostanes.

A composition or a food supplement of the disclosure may comprise any additive allowing improving in particular the preservation, the appearance, the taste, the formulation thereof. Thus, one or several additive(s) as those selected from preservative agents, colorants, flavors, disintegration agents, lubricant agents, coating or encapsulation agents may be incorporated therein.

A major application of a composition of the disclosure is nutraceutical, thus, such a composition or food supplement as defined hereinabove is advantageously in the form of gel capsules, capsules, tablets, pastilles or loose powder. Preferably, it is packaged in doses having a unit weight comprised between 1 mg and 1 g. In general, the galenic of the composition or of the supplement will be adapted to the considered individual and in particular depending on whether it is intended to a child or an adult.

A composition or a food supplement of the disclosure may be used to prevent the apparition of non-pathological age-related cognitive disorders or non-pathological cognitive disorders in children or young adults having been subjected to a prenatal stress. In the prevention of age-related cognitive disorders, the daily intake may be comprised between 2 to 5 mg/kg of body weight. In the prevention of cognitive disorders in children or young adults having been subjected to a prenatal stress, the daily intake may be comprised between 0.05 to 0.1 mg/kg of body weight. It has been noticed that an effect is observed even for very small daily intakes, provided that the duration of the treatment is proportionally extended.

The disclosure also concerns the use of a microalga to prepare a food supplement as previously defined. One or several preferred microalga(e) are selected from any one of the following taxons Pinguiophyceae, Chrysophyceae, Bacillariophyceae, Mamiellophyceae, Prymnesiophyceae, Haptophyceae, Coccolithophyceae, Isochrysidaceae and Phaeodactylaceae. Advantageously, the microalga is *Tisochrysis lutea* or *Phaeodactylum tricornutum*. Such microalgae will be selected because an appropriate extraction leads to an extract whose composition meets the definition of a composition of the disclosure. As example, such an extract may comprise the following fraction of fatty acids: the fatty acids, expressed in weight percentages with respect to the total extract, are in the form of free fatty acids between 4 and 55%, in the form of monoacyl glycerol between 0.5 and 10%, in the form of diacylglycerol between 0.4 and 15% and in the form of triacyl glycerol between 2 and 55%. These fatty acids are in the range of 5 to 20% (m/m) of the fatty acids from the omega-3 series and between 0.5 and 5%, of the fatty acids from the omega-6 series. More specifically, in particular, the fatty acids are ALA (α-linolenic acid) between 0.5 and 10%, SDA (stearidonic acid) between 0.5 and 10%, EPA (eicosapentaenoic acid) between 0.05 and 20%, DHA (docosahexaenoic acid) between 0.1 and 10%.

As previously indicated, one of the interests of a composition or of a food supplement lies in the method of preparation thereof and specifically the natural origin of its constituents all of which may be obtained from one single microalga. Depending on the used microalga, the formulation of the composition may be obtained directly with the extract. If such is not the case, the extract will be diluted to obtain the required concentrations according to the disclosure. Nonetheless, the disclosure is not limited to this implementation, thus, it may be considered that only one portion of the constituents is from a natural origin, the others being obtained through a chemical synthesis and/or that the constituents from a natural origin do not originate from the same source, for example, they are not produced from the same alga.

The measurement and the adjustment of the concentrations of the active ingredients in an extract, and in the composition or the obtained food supplement, are carried out using analytic techniques that fall within the general knowledges of those skilled in the art.

A method for producing a composition or a food supplement from a microalga culture is described hereinafter in more details.

According to a variant of the disclosure, said organisms are microalgae, such as those belonging to the taxons Pinguiophyceae, Chrysophyceae, Bacillariophyceae, Mamiellophyceae, Prymnesiophyceae, Haptophyceae, Coccolithophyceae, Isochrysidaceae, Phaeodactylaceae. These photosynthesis-capable microorganisms may be strictly autotrophic, mixotrophic or transiently heterotrophic. These organisms may be harvested in a natural or preferably cultivated environment.

By extract, it is referred to a fraction of the biomass derived from the photosynthesis-capable organisms obtained by a method allowing obtaining, whether directly or indirectly, a composition of the disclosure. These extracts have a composition, expressed in weight percentage with respect to the total extract, in proteins comprised between 5 and 30%, in lipids between 20 and 80%, between 0.1 and 2% of sterols, between 0.1 and 20% of chlorophyll.

More specifically, the lipophilic portion composing the extract, expressed in weight percentage with respect to the total extract, is constituted by saturated fatty acids between 15 and 45%, polyunsaturated acids between 5 and 20%, xanthophylls between 1 and 20% and phycoprostane between 0.0002 and 0.007%.

For the production of the extract according to the disclosure, the cells advantageously consist of microalgae cells of the species Tisochrysis lutea of the Isochrysidaceae family, or microalgae cells of the species Phaedactylum tricornutum of the Phaeodactylaceae family, produced by carbon autotrophy.

Production Method of the Microalgae

The microalgae are ideally cultivated in a controlled manner within adapted systems such as race-ways, open ponds or preferably in closed systems such as photobioreactors. The used photobioreactors may be of any existing type such as horizontal tubular photobioreactors, vertical such as so-called « green wall panel » systems, planar or column type photobioreactors. Preferably, the production of the biomass will be performed within a closed cultivation system, by zero-impact autotrophy on arable lands.

The production of the biomass is performed according to batch, fed-batch, continuous, semi-continuous, turbidostat or chemostat type culture management practices.

Obtainment of the Extracts of these Microalgae

The extracts derived from these microorganisms are preferably obtained after concentration of the biomass by elimination of all or part of water using chemical or physical processes such as centrifugation, filtration, flocculation, sedimentation, whether coupled or not, at drying steps by freeze-drying, vacuum-drying, drum-drying, atomization or any other process allowing lowering the water content of the biomass. Complementarily to these steps, cellular lysis processes may be implemented such as the applications of pressures, electric flows, shear forces, the use of enzymes, or any other processes allowing destructuring the tissues, organs, cells or organelles.

The interesting compounds of the biomass are extracted according to a solid-liquid extraction type process, which may use hypercritical fluids or subcritical fluids, which may involve co-treatments carried out in parallel or sequentially such as microwaves, ultrasounds, pressures, enzymes. The used solvents, whether pure or in a mixture, may consist of acetone, hexane, ethyl acetate, methyltetrahydrofuran, heptane, methanol, natural or branched oils, ethanol or any other solvent allowing extracting all or part of the hydrophobic and amphiphilic compounds.

The solvent or the mixture of solvents is separated from the residual biomass after extraction by centrifugation, filtration type processes and may be concentrated afterwards, or the solvent eliminated, by techniques such as vacuum evaporation or any other technique allowing for the selective evaporation of the considered solvent. The extract thus obtained has a lipophilic nature while including amphiphilic molecules.

Formulation as a Food Supplement

The formulation of the extract is performed with compatible matrices, enabling the dissolution thereof in order to obtain a homogeneous solution with the desired concentration of extract such as for example, vegetable oils such that olive oil, colza oil, linseed oil, sunflower oil, grape seed oil, palm oil and preferably MCT oils, and composed to about 70 weight % of a mixture of caprylic acid and capric acid, and preferably selected from coconut oil or palm oil, the whole being supplemented with molecules allowing increasing stability such as synthetic or natural antioxidants. The weight rates of incorporation of the matrices/additives in order to obtain the supplement may reach 95 weight % with respect to the weight of the food supplement, they are generally comprised between 15 and 80%, preferably between 35 and 45%.

The extract, but preferably the formulated composition or the obtained supplement, may be formulated in form of soft capsules, or may be formulated in form of powder, by any technique enabling the micro-encapsulation of the aqueous solution involving, or not, a support or a matrix allowing, or not, a homogeneous dispersibility thereof within a drinkable polar solution.

The extract or the supplement may be used alone or as an ingredient within a food complementation.

BRIEF DESCRIPTION OF THE DRAWINGS

The different embodiments of the disclosure are illustrated hereinbelow and their advantages set out in the following examples, with reference to the following figures:

FIG. 1 is a representation of the effects of the supplement of the disclosure on the locomotor activity, with the left-side diagram illustrating the effects on the spontaneous alternation deficits and the right-side diagram illustrating the effects on the locomotor activity.

FIG. 2 is a representation of the effects on the learning deficits induced by the D-Gal according to the MWM test.

FIG. 3 is a representation of the effects of the supplement and of DHA on the learning deficits induced by the D-Galactose.

FIG. 4 is a representation of the effects on the passive avoidance deficits induced by the D-Galactose in mice, with the effects on the step-down latency illustrated on the left-side diagram and on the escape latency illustrated on the right-side diagram, measured during the retention period.

FIG. 5 is a representation of the effects of the supplement and of DHA on the lipid peroxidation induced by the D-Galactose.

FIG. 6 is a representation of the effects of the supplement and of DHA on the expression of TNF-α in the cortex and the plasma induced by the D-Galactose, with the effect on the cortex on the left-side diagram and the effect on the plasma on the right-side diagram.

FIG. 7 is a representation of the effects of the supplement and of DHA on the expression of IL-6 in the cortex (left-side diagram) and the plasma (right-side diagram) induced by the D-Galactose.

FIG. 8 is a representation of the effect of the supplement on anxiety, in the test of locomotion at the center of the test space, day PPD46.

FIG. 9 is a representation of the effect of the supplement on the recognition memory, in the test of recognition of an object, day PPD47.

FIG. 10 is a representation of the effect of the supplement on the recognition memory, in the test of recognition of a new object.

FIG. 11 is a representation of the effects of the supplement of the disclosure on the locomotor activity, with the left-side diagram illustrating the effects on the spontaneous alternation deficits and the right-side diagram illustrating the effects on the locomotor activity.

FIG. 12 is a representation of the effects on the learning deficits induced by the D-Gal according to the MWM test.

FIG. 13 is a representation of the effects of the supplement on the learning deficits induced by the D-Galactose.

FIG. 14 is a representation of the effects on the passive avoidance deficits induced by the D-Galactose in mice, with the effects on the step-down latency illustrated on the left-side diagram and on the escape latency illustrated on the right-side diagram, measured during the retention period.

FIG. 15 is a representation of the effects of the supplement on the lipid peroxidation induced by the D-Galactose.

FIG. 16 is a representation of the effects of the supplement on the expression of TNF-α in the cortex and the plasma induced by the D-Galactose, with the effect on the cortex on the left-side diagram and the effect on the plasma on the right-side diagram.

FIG. 17 is a representation of the effects of the supplement on the expression of IL-6 in the cortex (left-side diagram) and the plasma (right-side diagram) induced by the D-Galactose.

DETAILED DESCRIPTION AND EXAMPLES

Example 1: Formulation of an Extract Containing the Constituents of a Composition of the Disclosure An extract is obtained according to any of the above-described techniques from the microalga Phaeodactylum tricornutum.

It is water-insoluble and is highly viscous preventing any handling at room temperature.

The extract and the palm oil are kept at room temperature (25±1° C.) for 24 h before preparation. The extract is transferred in a centrifuge tube including the oil such that the final net mass of the mixture is about 5 g and the mass proportion is such that the extract consists of 25% of the overall net mass of the mixture. The mixture is stirred for one unit using a so-called vortex mixing device. Stirring is repeated three times for each mixture. A homogeneous mixture is obtained.

Example 2: Test of a Natural Extract of the Microalga *Tisochrysis lutea* in the Context of the In Vivo Model on the Attenuation of the Deficits Induced by the Age-Related Cognitive Decline The food supplement of the disclosure is prepared from a Tisochrysis lutea extract which comprises in mg/g:

Omega-3 type fatty acids (ALA, SDA, EPA, DHA): 152.6±14.4;
Fucoxanthin: 20.0±4.0;
Sterols: 4.9±0.8;
Phycoprostane: 0.035±0.007.

The supplement is obtained by addition of coconut oil in a proportion of 360 mg±10 mg/g to said extract.

The supplement is incorporated into kibbles according to 3 different formulations such that the final concentrations of DHA in these batches of kibbles are equal to 0.5, 1.5 and 3.0% (m:m).

A commercial oily extract of microalgae comprising, as a fat fraction, only the fatty acids DHA 77% (m:m) and EPA 3% (m:m) is also tested; it is also incorporated into a batch of kibbles such that the final concentration of DHA in this batch of kibbles is equal to 3.1% (m:m).

An additional batch of kibbles is formulated only with the coconut oil, such that the vehicle concentration is equivalent to that of the other batches, namely 0.01% (m:m).

The five batches of kibbles thus obtained are referenced as described in Table 1 hereinbelow.

TABLE 1

| Formulated kibbles | Reference | [DHA] in % (m:m) |
|---|---|---|
| Coconut oil | A1 | 0 |
| Supplement | A2 | 0.5 |
| Supplement | A3 | 1.5 |
| Supplement | A4 | 3.0 |
| Commercial oily extract | A5 | 3.1 |

The considered in vivo model is the D-Galactose model applied to mice which is suitable for the study of the age-related cognitive decline. Indeed, this model mimics numerous behavioral and molecular characteristics of the cerebral ageing in rodents' models.

The D-Galactose is administered subcutaneously in a daily proportion of 150 mg/kg of mice wet weight, and the food supplement hereinabove is incorporated into a pellet, according to the following pattern:

Between day -14 and day 51, the supplement is administered by incorporation into food pellets;
Between day 1 and day 51, the D-Galactose is administered subcutaneously, five days a week;
Between days 43 and 51, three different behavioral tests are used to monitor the effects of the test compounds.

The effectiveness of the supplement is assessed according to the following parameters:

improvement of the learning deficits (spatial working memory: spontaneous alternation in the Y labyrinth according to the Y-maze test; spatial memory by the so-called « Morris Water Maze » and long-term contextual memory in the passive avoidance test), lipid peroxidation (LPO) rate in the hippocampus and effect on the neuro-inflammation markers IL6 and TNFα.

Improvement of the Learning Deficits

On day 43, all animals have been tested for the spontaneous alternation performance in the Y-maze (YM) test, via a spatial working memory index;

From day 44 to day 49, all animals have been tested for the spatial memory in the Morris Water Maze (MWM) test, via a spatial memory index;

From day 44 to day 49, all animals are tested via the MWM test to assess the spatial working memory;

On days 50 and 51, the long-term contextual memory of the animals is assessed using the step-by-step type passive avoidance process (STPA), through exercise and retention sessions, respectively;

On days 50 and 51, all animals are tested for the STPA task.

Lipid Peroxidation (LPO) Rate in the Hippocampus and Effect on the Neuro-Inflammation Markers IL6 and TNFα

On the 51th day, after the behavioral tests, the animals have been euthanized.

For all animals, trunk blood is collected and centrifuged to recover plasma and the brain is rapidly collected. The hippocampus and the cortex are dissected, the hippocampus is then used to determine the lipid peroxidation rates by a colorimetric method; the hemi-frontal cortex and the plasma are used to determine the level of the inflammatory biomarkers interleukin-6 (IL-6) and tumor necrosis factor alpha (TNF-α)

The quantification of the lipid peroxidation (LPO) rates has been carried out according to the modified and adapted procedure of Hermes-Lima et al. This method measures the capacity of the peroxidized lipids of the brain to oxidize a ferrous oxide and xylenol orange complex, set out in the presence of cumene hydroperoxide (HPC). The lipid peroxidation level is determined in HPC-equivalent according to the formula:

$$HPCE = A5801/A5802 \times [HPC \text{ (nmol)}]$$

and expressed in HPC-equivalent per wet tissue weight and in percentage with respect to the data obtained for the control group (D-Galactose+vehicle).

The IL6 and TNFα contents are quantified by means of ELISA tests with the following kits:

For the quantification of IL6: ThermoScientifique, EM2IL6

For the quantification of TNFα: ThermoScientifique, EMTNFA

For all tests, the cortex is homogenized after defrosting in a buffer of 50 mM Tris-150 mM NaCl, pH 7.5, and sonicated for 20 s. After centrifugation (16 100 g for 15 min, 4° C.), a supernatant or plasma are used for the ELISA tests in compliance with the instructions of the manufacturer of the ELISA tests. For each test, the absorbance is read at 450 nm and the concentration of the sample is calculated using the standard curve. The results are expressed in pg of marker per mg of wet tissue.

All values, except the passive avoidance latencies, are expressed as an average more or less the standard deviation of the measurement. Statistical analyses are performed separately for each compound using a unidirectional ANOVA (value F), followed by a Dunnett post-hoc multiple comparison test. The passive avoidance latencies do not follow a Gaussian distribution, since the upper limit times are fixed. Hence, they are analyzed using a Kruskal-Wallis non-parametric ANOVA (value H), followed by Dunn multiple comparison test. The values with $p<0.05$ are considered as statistically significant.

The tests are performed on 60 male mice, distributed in 6 groups of 10 mice, amongst which the group 1 is the negative control group and the groups 2-6 are the positive control groups:

the group 1 is the group to which a subcutaneous saline solution is administered instead of D-Galactose and kibbles A1;

the group 2 is the group to which D-Galactose and kibbles A1 are administered;

the group 3 is the group to which D-Galactose and kibbles A2 are administered;

the group 4 is the group to which D-Galactose and kibbles A3 are administered; and the group 5 is the group to which D-Galactose and kibbles A4 are administered; and the group 6 is the group to which D-Galactose and kibbles A5 are administered.

The calculation of the human equivalent daily dose, from the daily dose tested in mice is defined as follows by the FDA (Guidance, 2005): the daily dose in human expressed in mg/kg of body weight (HED Human) is equal to the daily dose in the animal expressed in mg/kg of body weight (HED Animal) multiplied by the ratio of the safety factor (Km Animal) in the considered animal and of the safety factor for humans (Km Human). Km Human is equal to 37 and Km Mice is equal to 3.

Effects on the Spatial Memory in the Y-Maze Spontaneous Alternation Test

The results are represented in FIG. 1, the first diagram (to the left) illustrating the effects of the supplement of the disclosure on the spontaneous alternation deficits and the second diagram (to the right) illustrating the effects of the supplement of the disclosure on the locomotor activity.

In FIG. 1: LOW, low dose of the supplement (A2); MED, medium dose of the supplement (A3); HI, high dose of the supplement (A4); N is comprised between 9 and 10 depending on the groups; * $p<0.05$, *** $p<0.0001$ vs. the saline solution/group Veh, # $p<0.05$, ## $p<0.01$, ### $p<0.0001$ vs. the group D-GAL 150/group Veh; Dunnett test.

It is observed that the treatment with D-Galactose has significantly altered the spatial working memory, in comparison with the mice treated with the saline solution.

The supplement A2 has not demonstrated any effect on the alternation behavior. The supplement A3 has quite significantly but partially attenuated the deficits induced by the chronic intoxication with D-Galactose. The supplement A4 has quite significantly and completely attenuated the deficits induced by the chronic intoxication with D-Galactose.

The treatment with DHA alone (according to A5) has quite significantly but partially alleviated the deficits induced by the chronic intoxication with D-Gal.

Surprisingly, it turns out that the preventive treatment with the supplement according to the disclosure has a more considerable positive effect (quite significant and complete attenuation of the deficits) in comparison with the treatment with DHA alone (quite significant and partial attenuation of the deficits), and that for the same dose of DHA.

Effects on the Learning Deficits Induced by the D-Gal According to the MWM Test

The results are represented in FIG. 2.

In FIG. 2: LOW, low dose of the supplement (A2); MED, medium dose of the supplement (A3); HI, high dose of the supplement (A4); N is comprised between 9 and 10 depending on the groups; * $p<0.05$,  $p<0.01$, * $p<0.0001$ vs. the saline solution/group Veh, ## $p<0.01$, ### $p<0.0001$ vs. the group D-GAL 150/group Veh; Bonferroni multiple comparison test after bidirectional ANOVA.

The chronic intoxication with D-Galactose has considerably altered the spatial learning, in comparison with the negative control group (saline solution/vehicle).

The supplement A2 has not demonstrated any effect on the alternation behavior.

The supplement A3 has quite significantly but partially attenuated the deficits induced by the chronic intoxication with D-Galactose.

The supplement A4 has quite significantly and completely attenuated the deficits induced by the chronic intoxication with D-Galactose.

The DHA alone according to A5 has quite significantly but partially alleviated the deficits induced by the chronic intoxication with D-Galactose.

Surprisingly, it turns out that the preventive treatment with the supplement according to the disclosure at the dose A4 has a more considerable positive effect (quite significant and complete attenuation of the deficits) in comparison with the treatment with DHA alone (quite significant and partial attenuation of the deficits), and that for the same dose of DHA.

Effects of the Supplement and of the DHA on the Learning Deficits Induced by the D-Galactose The results are represented in FIG. 3.

In FIG. 3: LOW, low dose of the supplement (A2); MED, medium dose of the supplement (A3); HI, high dose of the supplement (A4); N is comprised between 9 and 10 depending on the group; *** $p<0.0001$ vs. the saline solution/group Veh,/Veh; ### $p<0.0001$ vs. the group D-GAL 150/Veh; Bonferroni multiple comparison test after bidirectional ANOVA.

The chronic intoxication with D-Galactose has considerably altered the spatial learning, in comparison with the negative control group (saline solution/vehicle).

The supplement A2 has not demonstrated any effect on the alternation behavior.

The supplement A3 has quite significantly but partially attenuated the deficits induced by the chronic intoxication with D-Galactose.

The supplement A4 has quite significantly and completely alleviated the deficits induced by the chronic intoxication with D-Galactose.

The treatment with DHA alone according to A5 has quite significantly but partially alleviated the deficits induced by the chronic intoxication with D-Galactose.

Surprisingly, it turns out that the preventive treatment with the supplement according to the disclosure at the dose A4 has a more considerable positive effect (quite significant and complete attenuation of the deficits) in comparison with the treatment with DHA alone (quite significant and partial attenuation of the deficits), and that for the same dose of DHA. In addition, the preventive treatment with the supplement at the dose A3 has an effect (quite significant and partial attenuation of the deficits) that is identical to the treatment with DHA alone while the latter is two times more concentrated in DHA.

Effects on the Passive Avoidance Deficits Induced by the D-Galactose in Mice

The results are represented in FIG. 4, with the effects of the supplement of the disclosure on the step-down latency illustrated on the left-side diagram and on the escape latency illustrated on the right-side diagram, measured during the retention period.

In FIG. 4: LOW, low dose of the supplement (A2); MED, medium dose of the supplement (A3); HI, high dose of the supplement (A4). N is comprised between 9 and 10 depending on the groups; *** $p<0.0001$ vs. the saline solution/group Veh, ### $p<0.0001$ vs. the group D-GAL 150/group Veh; Dunnett test.

The chronic intoxication with D-Galactose has considerably altered the long-term contextual working memory, in comparison with the negative control group (saline solution/vehicle).

The supplement A2 has not demonstrated any effect on the long-term contextual memory.

The supplement A3 has allowed attenuating the deficits induced by the chronic intoxication with D-Galactose in a non-significant manner.

The supplement A4 has quite significantly and completely attenuated the deficits induced by the chronic intoxication with D-Galactose.

The treatment with DHA alone (according to A5) has allowed attenuating the deficits induced by the chronic intoxication with D-Galactose in a non-significant manner.

Surprisingly, it turns out that the preventive treatment with the supplement of the disclosure at the dose A4 has a more considerable positive effect (quite significant and complete attenuation of the deficits) in comparison with the treatment with DHA alone (non-significant attenuation of the deficits), and that for the same dose of DHA. In addition, the preventive treatment with the supplement at the dose A3 has an effect (non-significant attenuation of the deficits) that is identical to the treatment with DHA alone while the latter is two times more concentrated in DHA.

Effects of the Supplement and of the DHA on the Lipid Peroxidation Induced by the D-Galactose The results are represented in FIG. 5.

In FIG. 5: LOW, low dose of the supplement (A2); MED, medium dose of the supplement (A3); HI, high dose of the supplement (A4). N is comprised between 9 and 10 depending on the groups;  $p<0.01$, * $p<0.0001$ vs. the saline solution/group Veh, ## $p<0.01$, ### $p<0.0001$ vs. the group D-GAL 150/group Veh; Dunnett test.

The chronic intoxication with D-Galactose has considerably increased the oxidative stress, in comparison with the negative control group (saline solution/vehicle).

The supplement A2 has not demonstrated any effect on the lipid peroxidation induced by the chronic intoxication with D-Galactose.

The supplement A3 has quite significantly but partially reduced the oxidative stress induced by the chronic intoxication with D-Galactose.

The supplement A4 has quite significantly and completely reduced the oxidative stress induced by the chronic intoxication with D-Galactose.

The treatment with DHA alone according to A5 has not demonstrated any effect on the oxidative stress induced by the chronic intoxication with D-Galactose.

Surprisingly, it turns out that the preventive treatment with the supplement of the disclosure at the dose A4 has a more considerable positive effect (quite significant and complete attenuation of the oxidative stress) in comparison with the treatment with DHA alone, and that for the same dose of DHA.

Effects of the Supplement and of the DHA on the Induced Expression of TNF-α in the Cortex and the Plasma by the D-Galactose The results are represented in FIG. 6, with the effect on the cortex on the left-side diagram and the effect on the plasma on the right-side diagram.

In FIG. 6: LOW, low dose of the supplement (A2); MED, medium dose of the supplement (A3); HI, high dose of the supplement (A4); N is comprised between 9 and 10 depending on the groups; *** $p<0.0001$ vs. the saline solution/group Veh, ### $p<0.0001$ vs. the group D-GAL 150/group Veh; Dunnett test.

The chronic intoxication with D-Galactose has considerably increased in a significant manner the TNF-α in the cortex and the plasma, in comparison with the negative control group (saline solution/vehicle).

The supplements A2 and A3 have quite significantly but partially reduced the increase of the TNF-α induced by the chronic intoxication with D-Galactose in the cortex and the plasma.

The supplement A4 has quite significantly and completely reduced the level of the TNF-a in the cortex and the plasma.

The treatment with DHA alone according to A5 has quite significantly but partially reduced the increase of the TNF-α induced by the chronic intoxication with D-Galactose in the cortex and the plasma.

Surprisingly, it turns out that the preventive treatment with the supplement HI (A4) has a more considerable positive effect (quite significant and complete attenuation of the increase of the TNF-α in the cortex and in the plasma) in comparison with the treatment with DHA alone, and that for the same dose of DHA. In addition, the preventive treatments with the supplement at the doses A2 and A3 have effects in the case of the cortex and the plasma (quite significant attenuations of the increases) that are identical to the treatment with DHA alone while the latter is respectively six and two times more concentrated in DHA, in comparison with the preventive treatments with the supplement at the doses A2 and A3, respectively.

Effects of the Supplement and of the DHA on the Induced Expression of IL-6 in the Cortex and the Plasma by the D-Galactose The results are represented in FIG. 7, with the effect on the cortex on the left-side diagram and the effect on the plasma on the right-side diagram.

In FIG. 7: LOW, low dose of the supplement (A2); MED, medium dose of the supplement (A3); HI, high dose of the supplement (A4); N is comprised between 9 and 10 depending on the groups; *** $p<0.0001$ vs. the saline solution/group Veh, ### $p<0.0001$ vs. the group D-GAL 150/group Veh; Dunnett test.

The chronic intoxication with D-Galactose has considerably increased in a significant manner the IL-6 in the cortex and the plasma, in comparison with the negative control group (saline solution/vehicle).

The low-dose supplement (A2) has not demonstrated any effect on the concentration of IL-6 induced by intoxication with D-Galactose.

The medium-dose supplement (A3) has quite significantly but partially reduced the increase of the IL-6 content induced by the chronic intoxication with D-Galactose in the cortex and the plasma.

The high-dose supplement (A4) has quite significantly and completely reduced the IL-6 content in the cortex and the plasma, induced by the chronic intoxication with D-Galactose in the cortex and the plasma.

The treatment with DHA alone according to A5 has quite significantly but partially reduced the increase of the IL-6 induced by the chronic intoxication with D-Galactose in the cortex and the plasma.

Surprisingly, it turns out that the preventive treatment with the supplement HI according to A4 has a more considerable positive effect (quite significant and complete attenuation of the increase of the IL-6 in the cortex and in the plasma) in comparison with the treatment with DHA alone (quite significant and partial attenuation of the increase of the IL-6 in the cortex and in the plasma), and that for the same dose of DHA. In addition, the preventive treatment with the supplement at the dose A3 has an effect in the case of the cortex (non-significant attenuation of the deficits) that is identical to the treatment with DHA alone while the latter is two times more concentrated in DHA.

In conclusion:

The chronic intoxication with D-Galactose has quite significantly induced an alteration of the spatial working memory, of the long-term contextual memory and has prejudiced the spatial learning. The behavioral alterations are also related to biochemical alterations manifested in an increase of oxidative stress and in an induction of neuro-inflammatory processes.

The preventive treatment with the supplement of the disclosure is dose-dependent and has quite significantly and completely attenuated in the case of the strongest tested dose (the supplement D4) the deficits induced by the chronic intoxication with D-Galactose manifested in a behavioral alteration, an increase of oxidative stress and an activation of neuro-inflammatory processes.

The treatment with DHA alone (A5), and at an equivalent dose of DHA in comparison with the treatment with the supplement HI, has quite significantly but partially reduced the deficits induced by the chronic intoxication with D-Galactose manifested in a behavioral alteration, an increase of oxidative stress and an activation of neuro-inflammatory processes.

Surprisingly, the preventive treatment by the supplement is significantly more effective at an equivalent dose of DHA than the preventive treatment with DHA alone, with regards to the attenuation of the age-related cognitive decline on a murine model caused by a chronic intoxication with D-Galactose. In addition, the preventive treatment by the supplement, for doses of DHA that are two times lower, has positive effects which are identical to the treatment with DHA alone, while the latter is two times more concentrated in DHA, in the case of the decrease of the oxidative stress measured in the cortex (IL-6 and TNF-α), in the plasma (TNF-α), in the case of the long-term contextual memory and in the case of spatial learning. And, the preventive treatment by the supplement has positive effects which are identical to the treatment with DHA alone, while the latter is six times more concentrated in DHA, in the case of the decrease of the oxidative stress measured in the cortex (IL-6 and TNF-α) and the plasma (TNF-α).

Thus, by applying the formula for calculating the human equivalent daily dose, a preventive treatment of the age-related cognitive decline may be defined with the daily intake of 2 to 5 mg of supplement/kg of body weight.

Example 3: Test of an Extract of the Microalga *Tisochrysis lutea* in Young Female Rats Suffering from a Prenatal Stress In this example, the resolution of the cognitive deficits, the anxious behavior and the alteration of the recognition memory, induced in young female rats after a prenatal stress of the ancestry thereof, via the administration of a supplement based on an extract of the microalga Tisochrysis lutea corresponding to that used in Example 2, is studied Equipment and Methods The model used in this example is an acknowledged model for inducing prenatal stress in rats by immobilizing the pregnant female in a cylinder under a harsh lighting.

Pregnant female rats have been randomly assigned to prenatal stress group (SP) or to control groups (NS), individually put in plastic-made breeding cages, and have had ad libitum access to food and water, except during the behavioral tests time. The conditions within the cages are as follows: photoperiod 12 h of light/12 h of darkness cycle (light turned on at 7 AM), in a room at constant temperature (21° C.) and constant humidity (50%).

The prenatal stress procedure has been performed as described by Meunier et al. (2004). The immobilizations of the female rats have been the object of a semi-random constraining procedure. The animals have been place and retained in Plexiglas-made transparent ferret retainers (20 cm long, 7 cm diameter) under a bright light for a total period of 90 minutes a day, for 4 consecutive days. For the stress to be as unpredictable as possible, the 90 minutes forced immobilization period has been administered in the following manner: one single 90 min phase, two 45 min phases spaced by 4 h, two 60 and 30 min phases spaced by 4 h, or three 30 min phases spaced by 4 and 1 h, and that, at different times of the day.

Control mothers have also been manipulated, but have never been placed in the ferret retainers.

The treated female rats have been allowed to clear themselves naturally from the trap of the ferret retainers as of the day 1 after the birth (PPD1).

The litters have been weaned on PPD21. The rats have been separated from the mothers, identified according to their gender, weighted and rats of the same gender have been distributed in cages (3 rats per cage). The young rats within the same cage originated from different litters, in order to avoid any possible litter-related effect.

The conditions within the cages are as follows: photoperiod 12 h of light/12 h of darkness cycle (light turned on at 7 AM), in a room at constant temperature (21° C.) and constant humidity (50%), with ad libitum access to food and water, except during the behavioral tests time.

In each cage, the animals have received the same treatment. The animals have been tested randomly and in a double-blind manner.

Forty-eight (48) female rats have been used and grouped into four groups of animals, constituted in the following manner:

The group 1 is composed by 12 naïve female rats, that is to say whose ancestry has not been subjected to a prenatal stress, and receiving only 200 μL a day of the vehicle solution (reference: NS/Vehicle). Hence, this group is the control group;

The group 2 is composed by 12 naïve female rats, that is to say whose ancestry has not been subjected to a prenatal stress, and receiving 200 μL a day of the supplement (reference: p NS/Supplement);

The group 3 is composed by 12 female rats whose ancestry has been subjected to a prenatal stress, and receiving 200 μL a day of the vehicle solution (reference: SP/Vehicle);

The group 4 is composed by 12 female rats whose ancestry has been subjected to a prenatal stress, and receiving 200 μL a day of the supplement (reference: SP/Supplement);

The effectiveness of the supplement has been assessed 6 weeks after birth.

The supplement (one dose) has been administered by gavage once every day, 5 days a week. The administrations have started after weaning, namely after the postpartum day (PPD) 25, and has lasted until PPD46.

The daily intake was 25.7 mg of supplement per kg of rat body weight.

The animals have been subjected to behavioral tests during the period between the days PPD46 and PPD48, namely outside the period of treatment with the vehicle or the supplement. Hence, the effects that are therefore observed during the behavioral tests will be due to a treatment that is preventive in nature.

The behavioral tests are divided into one anxiety assessment session and two objects recognition sessions. The sessions are defined as follows:

Session 1, PPD 46: The rats have been individually placed in a square open space (50 cm×50 cm×50 cm×50 cm) made of blue-colored Plexiglas with a floor equipped with infrared light-emitting diodes. The rats have been accustomed to the test space during a 10 minute session and their displacements captured by an infrared camera and analyzed using the Ethovision® (Noldus) software. The activity has been analyzed according to the overall covered distance (m), and according to the percentage of presence in the 25 cm×25 cm central area defined by the software/these data report on the intensity of the anxious behavior (38).

Session 2, PPD 47: Two identical objects (50 mL plastic-made Eppendorf tube) have been placed at determined locations (on two opposite edges of the central area). Each rat has been placed within the test space and the exploratory activity recorded during a 10 minute session. The activity has been analyzed in terms of number of contacts with the objects and of duration of the contacts.

Session 3, PPD 48: The object of session 2 has been replaced with a new object (a plastic-made bottle cap) whose shape, texture, color differ from those of the familiar object. Each rat has been replaced in the test space and the exploratory activity has been recorded during a 10 minute session. The activity has been the object of an analysis similar to that described in session 2.

The preferential exploration index has been calculated as the ratio of the number (or duration) of contacts with the object of session 2, to the overall number (or duration) of contacts with both objects.

All values are expressed as an average more or less the standard deviation of the measurement. Statistical analyses are performed separately for each compound using a unidirectional ANOVA (value F), followed by a Dunnett post-hoc multiple comparison test.

The calculation of the human equivalent daily dose, from the daily dose tested in rats is defined as follows by the FDA (Guidance, 2005): the daily dose in human expressed in mg/kg of body weight (HED Human) is equal to the daily dose in the animal expressed in mg/kg of body weight (HED Animal) multiplied by the ratio of the safety factor (Km Animal) in the considered animal and of the safety factor for humans (Km Human). Km Human is equal to 37 and Km Rat is equal to 6.

The results are presented hereinafter.

Locomotion at the Center of the Test Space, Day PPD46, Effect of the Supplement on Anxiety The results are represented in FIG. 8.

In FIG. 8: Effects of the treatment on anxiety. N=12; *** $p<0.0001$ with respect to the treated group NS/vehicle; #### $p<0.0001$ with respect to the treated group SP/vehicle; Dunnett test.

The group SP/Vehicle, corresponding to the individuals having been subjected to a prenatal stress and preventively treated with the vehicle alone, has a percentage of displacements that is quite significantly higher within the peripheral area of the open test space in comparison with the group NS/Vehicle (the group that has not been subjected to a prenatal stress).

The group SP/supplement, corresponding to the individuals having been subjected to a prenatal stress and preventively treated with the supplement has a percentage of displacements that is quite significantly lower within the peripheral area of the open test space in comparison with the group SP/Vehicle (the group that has been subjected to a prenatal stress but not treated with the supplement). In addition, the percentage of displacements of the group SP/supplement is equivalent to that of the control group NS/vehicle.

A rate of displacements of the individuals in the peripheral area of the open test space that is higher than the control modality is the demonstration of an anxious behavior [63], via a protection mechanism based on the search for boundaries limiting the uncovered areas and is to be monitored.

Thus, the prenatal stress (PS) has induced a very significant anxious behavior.

Surprisingly, it turns out that the supplement has quite significantly and completely attenuated the anxious behavior induced by the prenatal stress.

Recognition Test, Day PPD47; Effect of the Supplement on the Recognition Memory in the Recognition of an Object The results are represented in FIG. 9.

During this session, the same object is exhibited twice to the individuals.

No statistical effect between the groups has been measured for this parameter.

Thus, the individuals of all groups have interacted in an equivalent manner when put in contact with identical objects and their interactions, both in terms of frequency and duration are equally distributed between the two objects (50%).

Recognition Test, Day PPD48 (new object); Effect of the Supplement on the Recognition Memory for the Test of Recognition of a New Object The results are represented in FIG. 10.

In FIG. 10: N=12; *** p<0.0001 with respect to the treated group NS/vehicle; #### p<0.0001 with respect to the treated group SP/vehicle; Dunnett test.

During this session, two different objects are exhibited to the individuals each once: one of the objects corresponds to the object exhibited during the session 2 and the other object is a new object.

The group SP/vehicle, corresponding to the individuals having been subjected to a prenatal stress and preventively treated with the vehicle alone, has a percentage of interactions, both in terms of frequency and duration, with the exhibited new object that is quite significantly lower in comparison with the group NS/Vehicle (the group that has not been subjected to a prenatal stress). And this percentage is equal to that of the session 2 obtained for all groups. Thus, the individuals of the group SP/vehicle have as many interactions with the ancient object as with the new object and therefore the individuals of this group do not recognize the ancient object exhibited during the session 2.

In contrast, the group SP/Supplement corresponding to the individuals having been subjected to a prenatal stress and preventively treated with the supplement, has a percentage of interactions, both in terms of frequency and duration, with the exhibited new object that is quite significantly higher in comparison with the group PS/Vehicle (the negative control group). And this percentage is higher than that of the session 2 obtained for all groups. Thus, the individuals of the group SP/Supplement have less interactions with the ancient object than with the new object, and therefore the individuals of this group recognize the ancient object exhibited during the session 2. In addition, the individuals of the group SP/Supplement have a percentage of interactions, both in terms of frequency and duration, with the exhibited new object that is equivalent with those of the groups NS/Vehicle and NS/Supplement.

Thus, the prenatal stress (PS) has induced very considerable recognition memory deficits in the case of the new object.

Surprisingly, it turns out that the supplement has allowed attenuating quite significantly and completely the recognition memory deficits induced by the prenatal stress.

In conclusion:

The treatment with the supplement has significantly and completely attenuated the anxious behavior as well as the recognition memory deficits induced by the prenatal stress.

The prenatal stress as practiced in this experiment significantly induces an anxious behavior, and quite significantly alters the recognition memory in young female rats.

Thus, by applying the formula for calculating the human equivalent daily dose, a preventive treatment attenuating the cognitive disorders caused by a prenatal stress may be defined with the daily intake of 0.05 to 0.1 mg of supplement/kg of body weight.

Example 4: Test of a Natural Extract of the Microal2a *Phaeodactylum tricornutum* in the Context of the In Vivo Model on the Attenuation of the Deficits Induced by the Age-Related Cognitive Decline The food supplement of the disclosure is prepared from a *Phaeodactylum tricornutum* extract which comprises in mg/g:

Omega-3 type fatty acids (ALA, SDA, EPA, DHA): 66.6 ±11.5;

Fucoxanthin: 20.0±4.0;

Sterols: 3.0±0.6;

Phycoprostane: 0.0025±0.0005.

The supplement is obtained by addition of coconut oil in a proportion of 410 mg±20 mg/g to said extract.

The supplement is incorporated into kibbles according to 4 different formulations such that the incorporated amounts of the supplement within the different batches of kibbles correspond to human equivalent daily doses as described in Table 2, and that, by dilution of the composition described hereinbelow in coconut oil with an equal final mass for all formulations.

The calculation of the human equivalent daily dose, from the daily dose tested in mice is defined as follows by the FDA (Guidance, 2005): the daily dose in human expressed in mg/kg of body weight (HED Human) is equal to the daily dose in the animal expressed in mg/kg of body weight (HED Animal) multiplied by the ratio of the safety factor (Km Animal) in the considered animal and of the safety factor for humans (Km Human). Km Human is equal to 37 and Km Mice is equal to 3.

An additional batch of kibbles is formulated only with the coconut oil, such that the vehicle concentration is equivalent to that of the other batches, namely 0.01% (m:m).

The five batches of kibbles thus obtained are referenced as described in Table 2 hereinbelow.

TABLE 2

| Formulated kibbles | Human equivalent ssdupplement dose (mg of supplement/ kg of body mass/day) | Reference |
| --- | --- | --- |
| Coconut oil (vehicle) | 0 | Veh. |
| Supplement | 1.7 | D1 |
| Supplement | 3.3 | D2 |
| Supplement | 4.2 | D3 |
| Supplement | 5.3 | D4 |

The considered in vivo model is the D-Galactose model applied to mice which is suitable for the study of the age-related cognitive decline. Indeed, this model mimics numerous behavioral and molecular characteristics of the cerebral ageing in rodents' models.

The D-Galactose is administered subcutaneously in a daily proportion of 150 mg/kg of mice wet weight, and the food supplement hereinabove is incorporated into a pellet, according to the following pattern:

Between day -28 and day 51, the supplement is administered by incorporation into food pellets;

Between day 1 and day 51, the D-Galactose is administered subcutaneously, five days a week;

Between days 43 and 51, three different behavioral tests are used to monitor the effects of the test compounds.

The effectiveness of the supplement is assessed according to the following parameters: improvement of the learning deficits (spatial working memory: spontaneous alternation in the Y labyrinth according to the Y-maze test; spatial memory by the so-called « Morris Water Maze» and long-term contextual memory in the passive avoidance test), lipid peroxidation (LPO) rate in the hippocampus and effect on the neuro-inflammation markers IL6 and TNFα.

Improvement of the Learning Deficits

On day 43, all animals have been tested for the spontaneous alternation performance in the Y-maze (YM) test, via a spatial working memory index;

From day 44 to day 49, all animals have been tested for the spatial memory in the Morris Water Maze (MWM) test, via a spatial memory index;

From day 44 to day 49, all animals are tested via the MWM test to assess the spatial working memory;

On days 50 and 51, the long-term contextual memory of the animals is assessed using the step-by-step type passive avoidance process (STPA), through exercise and retention sessions, respectively.

Lipid Peroxidation (LPO) Rate in the Hippocampus and Effect on the Neuro-Inflammation Markers IL6 and TNFα

On the 51th day, after the behavioral tests, the animals have been euthanized.

For all animals, trunk blood is collected and centrifuged to recover plasma and the brain is rapidly collected. The hippocampus and the cortex are dissected, the hippocampus is then used to determine the lipid peroxidation rates by a colorimetric method; the hemi-frontal cortex and the plasma are used to determine the level of the inflammatory biomarkers interleukin-6 (IL-6) and tumor necrosis factor alpha (TNF-α)

The quantification of the lipid peroxidation (LPO) rates has been carried out according to the modified and adapted procedure of Hermes-Lima et al. This method measures the capacity of the peroxidized lipids of the brain to oxidize a ferrous oxide and xylenol orange complex, set out in the presence of cumene hydroperoxide (HPC). The lipid peroxidation level is determined in HPC-equivalent according to the formula:

$$HPCE = A5801/A5802 \times [HPC\ (nmol)]$$

and expressed in HPC-equivalent per wet tissue weight and in percentage with respect to the data obtained for the control group (D-Galactose+vehicle).

The IL6 and TNFα contents are quantified by means of ELISA tests with the following kits:

For the quantification of IL6: ThermoScientifique, EM2IL6

For the quantification of TNFα: ThermoScientifique, EMTNFA

For all tests, the cortex is homogenized after defrosting in a buffer of 50 mM Tris-150 mM NaCl, pH 7.5, and sonicated for 20 s. After centrifugation (16 100 g for 15 min, 4° C.), a supernatant or plasma are used for the ELISA tests in compliance with the instructions of the manufacturer of the ELISA tests. For each test, the absorbance is read at 450 nm and the concentration of the sample is calculated using the standard curve. The results are expressed in pg of marker per mg of wet tissue.

All values, except the passive avoidance latencies, are expressed as an average more or less the standard deviation of the measurement. Statistical analyses are performed separately for each compound using a unidirectional ANOVA (value F), followed by a Dunnett post-hoc multiple comparison test. The passive avoidance latencies do not follow a Gaussian distribution, since the upper limit times are fixed. Hence, they are analyzed using a Kruskal-Wallis non-parametric ANOVA (value H), followed by Dunn multiple comparison test. The values with $p<0.05$ are considered as statistically significant.

The tests are performed on 72 male mice, distributed in 6 groups of 12 mice, amongst which the group 1 is the negative control group and the groups 2-6 are the positive control groups:

the group 1 is the group to which a subcutaneous saline solution is administered instead of D-Galactose and kibbles B1;

the group 2 is the group to which D-Galactose and kibbles B1 are administered;

the group 3 is the group to which D-Galactose and kibbles B2 are administered;

the group 4 is the group to which D-Galactose and kibbles B3 are administered; and the group 5 is the group to which D-Galactose and kibbles B4 are administered; and the group 6 is the group to which D-Galactose and kibbles B5 are administered.

Effects on the Spatial Memory in the Y-maze Spontaneous Alternation Test

The results are represented in FIG. 11, the first diagram (to the left) illustrating the effects of the supplement of the disclosure on the spontaneous alternation deficits and the second diagram (to the right) illustrating the effects of the supplement of the disclosure on the locomotor activity.

In FIG. 11: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; * $p<0.05$, *** $p<0.0001$ vs. the saline solution/group Veh, # $p<0.05$, ## $p<0.01$, ### $p<0.0001$ vs. the group D-GAL 150/group Veh; Dunnett test.

It is observed that the treatment with D-Galactose has significantly altered the spatial working memory, in comparison with the mice treated with the saline solution.

The supplement D1 has quite significantly but partially attenuated the deficits induced by the chronic intoxication with D-Galactose. The supplements D2, D3 and D44 have quite significantly and completely attenuated the deficits induced by the chronic intoxication with D-Galactose.

Effects on the Learning Deficits Induced by the D-Gal According to the MWM Test The results are represented in FIG. 12.

In FIG. 12: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; * $p<0.05$,  $p<0.01$, * $p<0.0001$ vs. the saline solution/group Veh, ## $p<0.01$, ### $p<0.0001$ vs. the group D-GAL 150/group Veh; Bonferroni multiple comparison test after bidirectional ANOVA.

The chronic intoxication with D-Galactose has considerably altered the spatial learning, in comparison with the negative control group (saline solution/vehicle).

The supplement D1 has quite significantly but partially attenuated the deficits induced by the chronic intoxication with D-Galactose.

The supplements D2, D3 and D4 have quite significantly and completely attenuated the deficits induced by the chronic intoxication with D-Galactose.

Effects of the Supplement on the Learning Deficits Induced by the D-Galactose The results are represented in FIG. 13.

In FIG. 13: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; *** $p<0.0001$ vs. the saline solution/group Veh, Neh; ### $p<0.0001$ vs. the group D-GAL 150/Veh; Bonferroni multiple comparison test after bidirectional ANOVA. "T", the time spent in the target quadrant; "O", the average time spent in the three other quadrants.

The chronic intoxication with D-Galactose has considerably altered the spatial learning, in comparison with the negative control group (saline solution/vehicle).

The supplements D1 and D2 have quite significantly but partially attenuated the deficits induced by the chronic intoxication with D-Galactose.

The supplements D3 and D4 have quite significantly and completely alleviated the deficits induced by the chronic intoxication with D-Galactose.

Effects on the Passive Avoidance Deficits Induced by the D-Galactose in Mice The results are represented in FIG. 14, with the effects of the supplement of the disclosure on the step-down latency illustrated on the left-side diagram and on the escape latency illustrated on the right-side diagram, measured during the retention period.

In FIG. 14: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; *** $p<0.0001$ vs. the saline solution/group Veh, ### $p<0.0001$ vs. the group D-GAL 150/group Veh; Dunnett test.

The chronic intoxication with D-Galactose has considerably altered the long-term contextual working memory, in comparison with the negative control group (saline solution/vehicle).

The supplement D1 has not demonstrated any effect on the long-term contextual memory.

The supplements D2, D3 and D4 have quite significantly and completely attenuated the deficits induced by the chronic intoxication with D-Galactose.

Effects of the Supplement on the Lipid Peroxidation Induced by the D-Galactose The results are represented in FIG. 15.

In FIG. 15: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups;  $p<0.01$, * $p<0.0001$ vs. the saline solution/group Veh, ## $p<0.01$, ### $p<0.0001$ vs. the group D-GAL 150/group Veh; Dunnett test.

The chronic intoxication with D-Galactose has considerably increased the oxidative stress, in comparison with the negative control group (saline solution/vehicle).

The supplement D1 has quite significantly but partially reduced the oxidative stress induced by the chronic intoxication with D-Galactose.

The supplements D2, D3 and D4 have quite significantly and completely reduced the oxidative stress induced by the chronic intoxication with D-Galactose.

Effects of the Supplement on the Induced Expression of TNF-α in the Cortex and the Plasma by the D-Galactose The results are represented in FIG. 16, with the effect on the cortex on the left-side diagram and the effect on the plasma on the right-side diagram.

In FIG. 16: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; *** $p<0.0001$ vs. the saline solution/group Veh, ### $p<0.0001$ vs. the group D-GAL 150/group Veh; Dunnett test.

The chronic intoxication with D-Galactose has considerably increased in a significant manner the TNF-α in the cortex and the plasma, in comparison with the negative control group (saline solution/vehicle).

The supplement D1 has quite significantly but partially reduced the increase of the TNF-α induced by the chronic intoxication with D-Gal in the brain and the plasma.

The supplement D2 has quite significantly and completely reduced the increase of the TNF-α induced by the chronic intoxication with D-Gal in the brain, but partially in the plasmas.

The supplement D3 has quite significantly but partially reduced the increase of the TNF-α induced by the chronic intoxication with D-Gal in the brain, and completely in the plasma.

The supplement D4 has quite significantly and completely reduced the increase of the TNF-α induced by the chronic intoxication with D-Gal in the brain and the plasma.

Effects of the Supplement on the Induced Expression of IL-6 in the Cortex and the Plasma by the D-Galactose The results are represented in FIG. 17, with the effect on the cortex on the left-side diagram and the effect on the plasma on the right-side diagram.

In FIG. 17: Sol. Saline/veh corresponds to the negative control (the group that has not been treated with D-galactose and fed with the kibbles formulated with the vehicle, coconut oil); DGal 150/Veh corresponds to the positive control (the group that has been treated with D-Galactose and fed with the kibbles formulated with the vehicle, coconut oil); D1, D2, D3 and D4 increasing doses of the supplement; N is comprised between 11 and 12 depending on the groups; *** $p<0.0001$ vs. the saline solution/group Veh, ### $p<0.0001$ vs. the group D-GAL 150/group Veh; Dunnett test.

The chronic intoxication with D-Galactose has considerably increased in a significant manner the IL-6 in the cortex and the plasma, in comparison with the negative control group (saline solution/vehicle).

The supplements D1 and D2 have quite significantly but partially reduced the increase of the IL-6 induced by the chronic intoxication with D-Gal in the brain and the plasmas.

The supplements D3 and D4 have quite significantly and completely reduced the increase of the IL-6 induced by the chronic intoxication with D-Gal in the brain and the plasma.

In Conclusion

The chronic intoxication with D-Galactose has quite significantly induced an alteration of the spatial working memory, of the long-term contextual memory and has prejudiced the spatial learning. The behavioral alterations are also related to biochemical alterations manifested in an increase of oxidative stress and in an induction of neuro-inflammatory processes.

The preventive treatment with the supplement of the disclosure is dose-dependent and has quite significantly and completely attenuated in the case of the strongest tested dose (the supplement D4) the deficits induced by the chronic intoxication with D-Galactose manifested in a behavioral alteration, an increase of oxidative stress and an activation of neuro-inflammatory processes. And in the cases of the intermediate lower doses (the supplements D2 and D3), the supplement of the disclosure has quite significantly and completely attenuated the deficits induced by the chronic intoxication with D-Galactose manifested in the spatial working memory, an increase of oxidative stress and an activation of neuro-inflammatory processes.

Thus, by applying the formula for calculating the human equivalent daily dose, a preventive treatment of the age-related cognitive decline may be defined with the daily intake of 1.7 to 5.3 mg of supplement/kg of body weight.

The invention claimed is:

1. A tablet, capsule, capsule gel, or pastille consisting essentially of coconut oil and/or palm oil; fucoxanthin; stearidonic acid, eicosapentaenoic acid and/or docosahexaenoic acid; phytosterols; and phytoprostanes, isoprostanes and/or neuroprostanes.

2. The tablet, capsule, capsule gel, or pastille according to claim 1, consisting essentially of:
    50 to 250 mg/g of the stearidonic acid, eicosapentaenoic acid and/or docosahexaenoic acid;
    10 to 50 mg/g of the fucoxanthin;
    1 to 20 mg/g of the phytosterols; and
    2 to 100 µg/g of the phytoprostanes, isoprostanes and/or neuroprostanes.

3. The tablet, capsule, capsule gel, or pastille according to claim 1, consisting essentially of:
    50 to 200 mg/g of the stearidonic acid, eicosapentaenoic acid and/or docosahexaenoic acid;
    10 to 30 mg/g of the fucoxanthin;
    1 to 8 mg/g of the phytosterols; and
    2 to 50 µg/g of the phytoprostanes, isoprostanes and/or neuroprostanes.

4. The tablet, capsule, capsule gel, or pastille according to claim 1, consisting essentially of:
    50 to 170 mg/g of the stearidonic acid, eicosapentaenoic acid and/or docosahexaenoic acid;
    10 to 25 mg/g of the fucoxanthin;
    1 to 6 mg/g of the phytosterols; and
    2 to 40 µg/g of the phytoprostanes, isoprostanes and/or neuroprostanes.

5. The tablet, capsule, capsule gel, or pastille according to claim 1, wherein the total weight of the coconut oil and/or palm oil; fucoxanthin; stearidonic acid, eicosapentaenoic acid and/or docosahexaenoic acid; phytosterols; and phytoprostanes, isoprostanes and/or neuroprostanes is between 10 mg and 1 g.

* * * * *